(12) United States Patent
O'Neil et al.

(10) Patent No.: US 7,790,405 B2
(45) Date of Patent: Sep. 7, 2010

(54) SOLUTION PHASE BIOPANNING METHOD USING ENGINEERED DECOY PROTEINS

(75) Inventors: Karyn O'Neil, Kennett Square, PA (US); Raymond Sweet, Bryn Mawr, PA (US); George Heavner, Malvern, PA (US)

(73) Assignee: Centocor, Inc., Malvern, PA (US)

( * ) Notice: Subject to any disclaimer, the term of this patent is extended or adjusted under 35 U.S.C. 154(b) by 400 days.

(21) Appl. No.: 11/112,701

(22) Filed: Apr. 22, 2005

(65) Prior Publication Data

US 2005/0239140 A1    Oct. 27, 2005

Related U.S. Application Data

(60) Provisional application No. 60/565,674, filed on Apr. 26, 2004, provisional application No. 60/565,633, filed on Apr. 26, 2004.

(51) Int. Cl.
*G01N 33/53* (2006.01)

(52) U.S. Cl. .................. 435/7.2; 435/7.93; 435/328; 424/133.1; 424/139.1; 424/144.1; 530/387.3; 530/387.9

(58) Field of Classification Search .................. None
See application file for complete search history.

(56) References Cited

U.S. PATENT DOCUMENTS

| | | | |
|---|---|---|---|
| 5,223,427 A * | 6/1993 | Edgington et al. | .......... 435/337 |
| 5,853,724 A | 12/1998 | Garrity et al. | |
| 6,376,170 B1 | 4/2002 | Burton et al. | |
| 6,589,758 B1 | 7/2003 | Zhu | |

FOREIGN PATENT DOCUMENTS

| WO | WO9640921 A1 | 12/1996 |
|---|---|---|
| WO | WO9953049 A1 | 10/1999 |
| WO | WO0202773 A2 | 1/2002 |

OTHER PUBLICATIONS

Zhou et al., Proc. Natl. Acad. Sci. USA, 2002, 99:5241-5246.*
Carson et al., Blood, 1987, 70:490-493.*
Treacy G., Human and Experimental Toxicology, 2000, 19:226-228, abstract only.*
Lawson et al., J. Clin. Invest. 1997, 99:1729-1738.*
Horn, IR et al. "Selection of phage-displayed Fab antibodies on the active conformation of Ras yields a high affinity conformation . . . " FEBS Lett. 463:115-120, Dec. 10, 1999.
Hoogenboom, HR & Chames, P. Natural and desinger binding sites made by phage display technology Immunol Today 21(8): 371-378, 2000.
Huang, M et al. The mechanism of an inhibitory antibody on TF-initiated blood coagulation revealed by crystal structures . . . J Mol Biol 275:873-894, 1998.
Kretzschmar, T & von Rueden, T. "Antibody discovery: phage display" Curr Opin Biotechnol 13:598-602, Oct. 31, 2002.
Ke, S-H. Distinguishing the Specificities of Closely Related Proteases J Biol Chem 272(26): 16603-9, Jun. 27, 1997.
Kirkham, PM et al. "Towards the design of an antibody that recognizes a specific epitope" J Mol Biol 285:909-'5, 1999.
Osbourn, JK. "Pathfinder selection: in situ isolation of novel antibodies" Immunotechnol 3:293-302, 1998.
Parsons, HL et al. "Directing phage selections trowards specific epitopes" Protein Engineering 9(11): 1043-1049, 1996.
Tsui, P. et al. Progressive epitope-blocked panning of a phage library for isolation of human RSV antibodies. J Immunological Methods 263(2002): 123-132, 2002.
Van Ewijk, W et al. "Subtractive isolation of phage-displayed single-chain antibodies . . . " Proc Natl Acad Sci USA 94:3903-3908, Apr. 1997.

* cited by examiner

*Primary Examiner*—Michael Szperka
(74) *Attorney, Agent, or Firm*—Kenneth J. Dow

(57) ABSTRACT

The invention relates to a method of directing selection of biological therapeutic molecules to specific functional domains of the target biologic molecule. Selection is directed by the use of closely related molecules, where one is a decoy and the other contains the targeted domain or epitope. The invention is based on the use of physical data, which may be combined with derived data, to ascertain that the decoy and the target differ only in the specific functional domain or epitope where the binding will be directed.

6 Claims, 10 Drawing Sheets

*Fig. 2*

Figure 1:
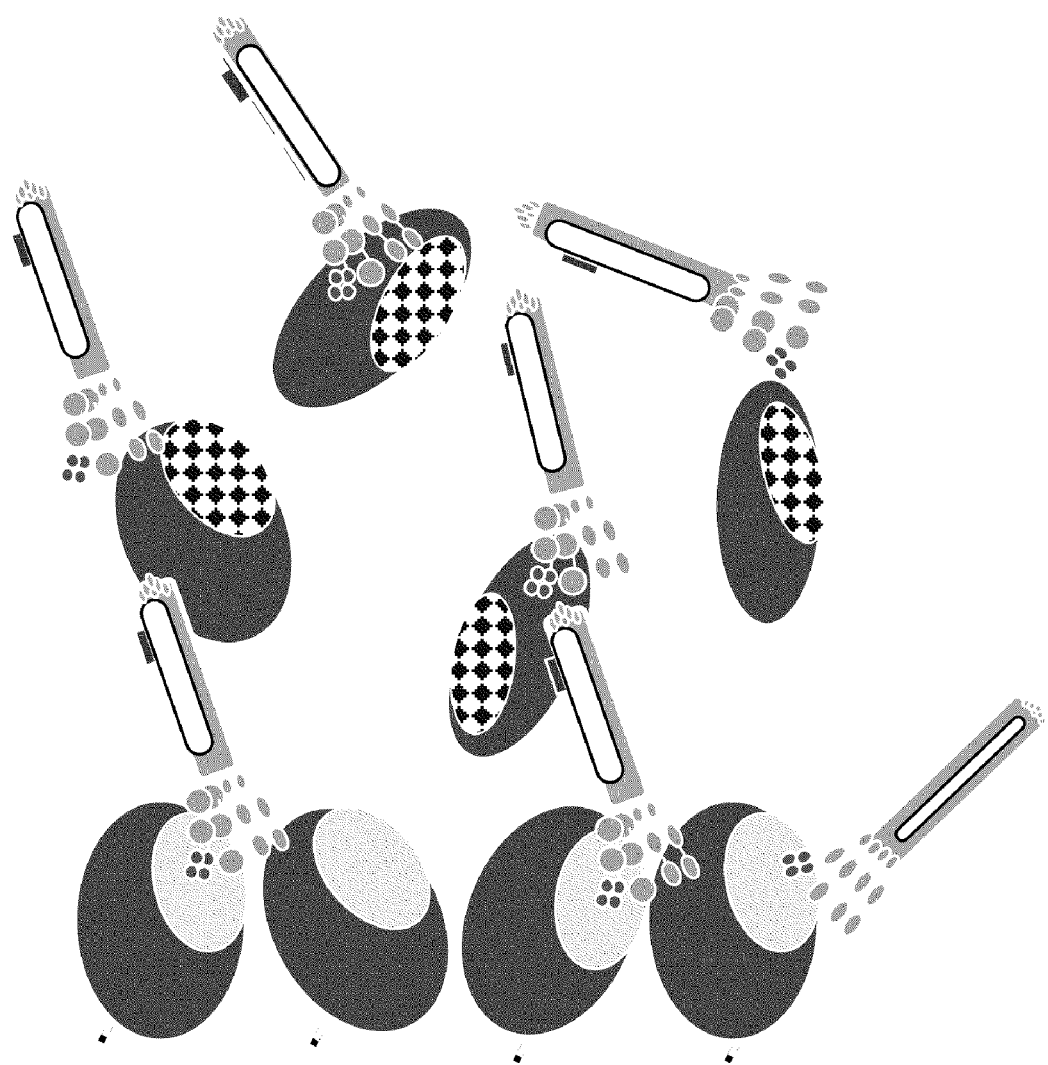

| PHD | SEQ ID NO: | Frame-work | Heavy Chain | | | SEQ ID NO: | Frame-work | Light Chain | | |
|---|---|---|---|---|---|---|---|---|---|---|
| | | | CDR1 | CDR2 | CDR3 | | | CDR1 | CDR2 | CDR3 |
| 103 | 2 | VH5 | GYSFSNSWIA | GIIGPGHSYTKYSPSFQG | INMGYFDY | 3 | V$_{kappa}$3 | SGDSLGLKKFVS | DDSNRPS | GTYDQTIGHDV |
| 104 | 4 | VH5 | YSFTSNWIG | WIYPSDSMTRYSPSFQG | YLFGLFDN | 5 | V$_{kappa}$3 | SGDNLGSYYVS | NDNNRPS | ATYDSSTD |
| 126 | 6 | VH5 | YSFSNYWIG | FIDPDDSDTNYSPSFQG | ALYMQGGSFDS | 7 | V$_{kappa}$3 | SGDNLGSYYVS | RDTDRPS | QSYDYGVSNQ |
| 127 | 8 | VH5 | YSFTNSWIS | IIDPDDSYTSYSPSFQG | GAGYGRMFGDV | 9 | V$_{kappa}$3 | SGDNLGSYYAS | QDDNRPS | GAYTYSTSW |
| 130 | 10 | VH2 | GLSLSTSGVGVGLIYSNDDKRYSTSLKT | | YKQETIDY | 11 | V$_{kappa}$3 | SGDNLGEKYAY | DDNNR | QSYDIEIT |

Framework Sequences:

VH5: QVQLVQSGAEVKKPGESLKISCKGS CDR1 WVRQMPGKGLEWMG CDR2 SISTAYLQWSSLKASDTAMYYCAR CDR3 WGQGTLVTVSS

VH2: QVQLKESGPALVKPTQTLTLTCTFS CDR1 WIRQPPGKALEWLA CDR2 QVTISADK RLTISKDTSKNQVVLTMTNMDPVDTATYYCAR CDR3 WGQGTLVTVSS

V$_{kappa}$3: DIELTQPPSVSVAPGQTARISC CDR1 WYQQKPGQAPVLVIY CDR2 GIPERFSGSNSGNTATLTISGTQAEDEADYYC CDR3 VFGGGTKLTVLG

Fig. 5

```
                    1                                                50
    IL-13 dog    (1) -----PVTPSPTLKELIEEIVNITQN-QASLCNGSMVWSVNLTA-GMYCA
    IL-13 human  (1) ----GPVPPSTALRELIEELVNITQNQKAPLCNGSMVWSINLTA-GMYCA
    IL-13 mouse  (1) GPVPRVSLPLTLKELIEELSNITQDQTP-LCNGSMVWSVDLAA-GGFCV
    IL-13 pig    (1) ---GPVPPHSTALKELIEELVNITQNQKTPLCNGSMVWSVNLTTSMQYCA
    IL-13 rat    (1) GPVRRTSPPVALRELIEELSNITQDQKTSLCNSSMVWSVDLTA-GGFCA
    IL-13 bovine (1) -----PVPSATALKELIEELVNITQNQKVPLCNGSMVWSINLTS-SMYCA 51                                               100
    IL-13 dog   (44) ALESLINVSDCSAIQRTQRMKALCSQKPAAGQISSERSRITKIEVIQLV
    IL-13 human (46) ALESLINVSGCSAIEKTQRMLSGFCPHKVSAGQFSSLHVRDTKIEVAQFV
    IL-13 mouse (49) ALDSLTNIGNCNAIYRTQRILHGLCNRKAPTTVSS---LPDTKIEVAHFI
    IL-13 pig   (48) ALESLINISDCSAIQKTQRMLSALCSHKPPSEQVPGKHIRDTKIEVAQFV
    IL-13 rat   (50) ALESLTNISSCNAIHRTQRILNGLCNQKASDVASS---PPDTKIEVAQFI
    IL-13 bovine(45) ALDSLISISNCSVIQRTKKMLNALCPHKPSAKQVSSEYVRDTKIEVAQFLL 101       117
    IL-13 dog   (94) KNLLTYVRGVYRHGNF-
    IL-13 human (96) KDLLHLKKLFREGRFN
    IL-13 mouse (96) TKLLSYTKQLFRHGPF-
    IL-13 pig   (98) KDLLKHLRMIFRHG---
    IL-13 rat   (97) SKLLNYSKQLFRYG---
    IL-13 bovine(95) KDLLRHSRIVFRNERFN
```

FIG. 6A

| | | FR_SIDE | FR_TOTAL | | | FR_SIDE | FR_TOTAL |
|---|---|---|---|---|---|---|---|
| 1 | HIS1 | 0.46 | 0.58 | 31 | ASP31 | 0.28 | 0.18 |
| 2 | LYS2 | 0.42 | 0.36 | 32 | ILE32 | 0.01 | 0.06 |
| 3 | CYS3 | 0.54 | 0.67 | 33 | PHE33 | 0.08 | 0.21 |
| 4 | ASP4 | 0.53 | 0.41 | 34 | ALA34 | 0.25 | 0.42 |
| 5 | ILE5 | 0.95 | 0.76 | 35 | ALA35 | 0.19 | 0.32 |
| 6 | THR6 | 0.23 | 0.17 | 36 | SER36 | 0.98 | 0.86 |
| 7 | LEU7 | 0.04 | 0.03 | 37 | LYS37 | 0.76 | 0.78 |
| 8 | GLN8 | 0.57 | 0.42 | 38 | ASN38 | 0.83 | 0.65 |
| 9 | GLU9 | 0.72 | 0.50 | 39 | THR39 | 0.19 | 0.42 |
| 10 | ILE10 | 0.00 | 0.00 | 40 | THR40 | 0.59 | 0.51 |
| 11 | ILE11 | 0.09 | 0.07 | 41 | GLU41 | 0.39 | 0.34 |
| 12 | LYS12 | 0.49 | 0.39 | 42 | LYS42 | 0.80 | 0.60 |
| 13 | THR13 | 0.00 | 0.00 | 43 | GLU43 | 0.52 | 0.36 |
| 14 | LEU14 | 0.00 | 0.00 | 44 | THR44 | 0.38 | 0.28 |
| 15 | ASN15 | 0.64 | 0.46 | 45 | PHE45 | 0.04 | 0.03 |
| 16 | SER16 | 0.51 | 0.39 | 46 | CYS46 | 0.00 | 0.00 |
| 17 | LEU17 | 0.01 | 0.04 | 47 | ARG47 | 0.06 | 0.04 |
| 18 | THR18 | 0.11 | 0.29 | 48 | ALA48 | 0.02 | 0.01 |
| 19 | GLU19 | 1.16 | 0.97 | 49 | ALA49 | 0.00 | 0.00 |
| 20 | GLN20 | 0.11 | 0.13 | 50 | THR50 | 0.21 | 0.17 |
| 21 | LYS21 | 0.56 | 0.50 | 51 | VAL51 | 0.02 | 0.03 |
| 22 | THR22 | 0.01 | 0.10 | 52 | LEU52 | 0.00 | 0.00 |
| 23 | LEU23 | 0.55 | 0.53 | 53 | ARG53 | 0.65 | 0.52 |
| 24 | CYS24 | 0.01 | 0.00 | 54 | GLN54 | 0.60 | 0.47 |
| 25 | THR25 | 0.07 | 0.05 | 55 | PHE55 | 0.02 | 0.04 |
| 26 | GLU26 | 0.89 | 0.72 | 56 | TYR56 | 0.07 | 0.06 |
| 27 | LEU27 | 0.20 | 0.16 | 57 | SER57 | 0.51 | 0.57 |
| 28 | THR28 | 0.48 | 0.48 | 58 | HIS58 | 0.80 | 0.73 |
| 29 | VAL29 | 0.01 | 0.03 | 59 | HIS59 | 0.17 | 0.13 |
| 30 | THR30 | 0.24 | 0.19 | 60 | GLU60 | 0.59 | 0.41 |

*Fig. 6B*

|    |        | FR_SIDE | FR_TOTAL |
|----|--------|---------|----------|
| 61 | LYS61  | 0.85    | 0.78     |
| 62 | ASP62  | 0.19    | 0.16     |
| 63 | THR63  | 1.02    | 0.87     |
| 64 | ARG64  | 0.69    | 0.62     |
| 65 | CYS65  | 0.01    | 0.00     |
| 66 | LEU66  | 0.41    | 0.30     |
| 67 | GLY67  | -       | 0.30     |
| 68 | ALA68  | 0.84    | 0.87     |
| 69 | THR69  | 0.59    | 0.50     |
| 70 | ALA70  | 1.08    | 0.77     |
| 71 | GLN71  | 0.77    | 0.63     |
| 72 | GLN72  | 0.27    | 0.20     |
| 73 | PHE73  | 0.59    | 0.46     |
| 74 | HIS74  | 0.77    | 0.59     |
| 75 | ARG75  | 0.27    | 0.22     |
| 76 | HIS76  | 0.02    | 0.02     |
| 77 | LYS77  | 0.65    | 0.51     |
| 78 | GLN78  | 0.42    | 0.33     |
| 79 | LEU79  | 0.03    | 0.02     |
| 80 | ILE80  | 0.09    | 0.07     |
| 81 | ARG81  | 0.71    | 0.59     |
| 82 | PHE82  | 0.30    | 0.23     |
| 83 | LEU83  | 0.00    | 0.00     |
| 84 | LYS84  | 0.47    | 0.39     |
| 85 | ARG85  | 0.59    | 0.47     |
| 86 | LEU86  | 0.00    | 0.00     |
| 87 | ASP87  | 0.04    | 0.03     |
| 88 | ARG88  | 0.58    | 0.54     |
| 89 | ASN89  | 0.15    | 0.13     |
| 90 | LEU90  | 0.00    | 0.00     |
| 91 | TRP91  | 0.26    | 0.23     |
| 92 | GLY92  | -       | 0.56     |
| 93 | LEU93  | 0.02    | 0.04     |
| 94 | ALA94  | 0.00    | 0.03     |

Fig. 6B continued

|     |        | FR_SIDE | FR_TOTAL |
|-----|--------|---------|----------|
| 95  | GLY95  | -       | 0.81     |
| 96  | LEU96  | 0.34    | 0.26     |
| 97  | ASN97  | 0.87    | 0.85     |
| 98  | SER98  | 0.75    | 0.52     |
| 99  | CYS99  | 0.03    | 0.32     |
| 100 | PRO100 | 0.47    | 0.43     |
| 101 | VAL101 | 0.12    | 0.29     |
| 102 | LYS102 | 0.63    | 0.67     |
| 103 | GLU103 | 0.23    | 0.26     |
| 104 | ALA104 | 1.04    | 0.84     |
| 105 | ASN105 | 0.69    | 0.56     |
| 106 | GLN106 | 0.47    | 0.45     |
| 107 | SER107 | 0.21    | 0.16     |
| 108 | THR108 | 0.30    | 0.24     |
| 109 | LEU109 | 0.00    | 0.00     |
| 110 | GLU110 | 0.48    | 0.39     |
| 111 | ASN111 | 0.66    | 0.49     |
| 112 | PHE112 | 0.00    | 0.01     |
| 113 | LEU113 | 0.04    | 0.03     |
| 114 | GLU114 | 0.78    | 0.56     |
| 115 | ARG115 | 0.53    | 0.43     |
| 116 | LEU116 | 0.02    | 0.02     |
| 117 | LYS117 | 0.49    | 0.38     |
| 118 | THR118 | 0.74    | 0.59     |
| 119 | ILE119 | 0.36    | 0.29     |
| 120 | MET120 | 0.00    | 0.00     |
| 121 | ARG121 | 0.53    | 0.44     |
| 122 | GLU122 | 0.85    | 0.62     |
| 123 | LYS123 | 0.18    | 0.14     |
| 124 | TYR124 | 0.51    | 0.41     |
| 125 | SER125 | 0.71    | 0.47     |
| 126 | LYS126 | 0.65    | 0.68     |
| 127 | CYS127 | 0.13    | 0.35     |
| 128 | SER128 | 0.57    | 0.68     |
| 129 | SER129 | 0.87    | 1.20     |

FIG. 7A.

|   |         | FR_SIDE | FR_AREA |   |         | FR_SIDE | FR_AREA |
|---|---------|---------|---------|---|---------|---------|---------|
| 1  | PRO1   | 0.51 | 0.69 | 31 | TRP31  | 0.21 | 0.17 |
| 2  | PRO2   | 0.12 | 0.45 | 32 | SER32  | 0.53 | 0.44 |
| 3  | SER3   | 0.73 | 0.50 | 33 | ILE33  | 0.44 | 0.47 |
| 4  | THR4   | 1.11 | 0.93 | 34 | ASN34  | 0.30 | 0.36 |
| 5  | ALA5   | 0.39 | 0.30 | 35 | LEU35  | 0.23 | 0.21 |
| 6  | LEU6   | 0.06 | 0.07 | 36 | THR36  | 0.72 | 0.78 |
| 7  | ARG7   | 0.79 | 0.66 | 37 | ALA37  | 1.07 | 0.91 |
| 8  | GLU8   | 0.76 | 0.54 | 38 | GLY38  | -    | 0.32 |
| 9  | LEU9   | 0.03 | 0.02 | 39 | MET39  | 0.71 | 0.57 |
| 10 | ILE10  | 0.20 | 0.15 | 40 | TYR40  | 0.40 | 0.38 |
| 11 | GLU11  | 0.84 | 0.72 | 41 | CYS41  | 0.54 | 0.41 |
| 12 | GLU12  | 0.33 | 0.32 | 42 | ALA42  | 0.41 | 0.22 |
| 13 | LEU13  | 0.00 | 0.03 | 43 | ALA43  | 0.23 | 0.14 |
| 14 | VAL14  | 0.28 | 0.19 | 44 | LEU44  | 0.07 | 0.05 |
| 15 | ASN15  | 0.73 | 0.53 | 45 | GLU45  | 0.14 | 0.10 |
| 16 | ILE16  | 0.16 | 0.14 | 46 | SER46  | 0.15 | 0.09 |
| 17 | THR17  | 0.00 | 0.03 | 47 | LEU47  | 0.03 | 0.02 |
| 18 | GLN18  | 0.64 | 0.60 | 48 | ILE48  | 0.08 | 0.06 |
| 19 | ASN19  | 0.88 | 0.73 | 49 | ASN49  | 0.34 | 0.24 |
| 20 | GLN20  | 0.60 | 0.60 | 50 | VAL50  | 0.06 | 0.05 |
| 21 | LYS21  | 0.75 | 0.60 | 51 | SER51  | 0.00 | 0.00 |
| 22 | ALA22  | 0.98 | 0.75 | 52 | GLY52  | -    | 0.00 |
| 23 | PRO23  | 0.21 | 0.17 | 53 | CYS53  | 0.34 | 0.33 |
| 24 | LEU24  | 0.32 | 0.23 | 54 | SER54  | 0.24 | 0.54 |
| 25 | CYS25  | 0.70 | 0.49 | 55 | ALA55  | 0.51 | 0.50 |
| 26 | ASN26  | 0.69 | 0.50 | 56 | ILE56  | 0.03 | 0.12 |
| 27 | GLY27  | -    | 0.27 | 57 | GLU57  | 1.29 | 1.10 |
| 28 | SER28  | 0.12 | 0.12 | 58 | LYS58  | 0.62 | 0.47 |
| 29 | MET29  | 0.31 | 0.24 | 59 | THR59  | 0.41 | 0.41 |
| 30 | VAL30  | 0.21 | 0.14 | 60 | GLN60  | 0.91 | 0.77 |

FIG. 7B.

| | | FR_SIDE | FR_AREA |
|---|---|---|---|
| | | -------- | -------- |
| 61 | ARG61 | 0.61 | 0.50 |
| 62 | MET62 | 0.08 | 0.13 |
| 63 | LEU63 | 0.00 | 0.00 |
| 64 | SER64 | 0.13 | 0.16 |
| 65 | GLY65 | - | 0.53 |
| 66 | PHE66 | 0.04 | 0.04 |
| 67 | CYS67 | 0.16 | 0.17 |
| 68 | PRO68 | 0.76 | 0.66 |
| 69 | HIS69 | 0.01 | 0.01 |
| 70 | LYS70 | 0.25 | 0.25 |
| 71 | VAL71 | 0.82 | 0.72 |
| 72 | SER72 | 0.04 | 0.03 |
| 73 | ALA73 | 0.02 | 0.01 |
| 74 | GLY74 | - | 0.40 |
| 75 | GLN75 | 0.67 | 0.75 |
| 76 | PHE76 | 0.34 | 0.35 |
| 77 | SER77 | 0.00 | 0.01 |
| 78 | SER78 | 0.73 | 0.74 |
| 79 | LEU79 | 0.82 | 0.78 |
| 80 | HIS80 | 0.85 | 0.65 |
| 81 | VAL81 | 0.46 | 0.43 |
| 82 | ARG82 | 0.39 | 0.33 |
| 83 | ASP83 | 0.95 | 0.69 |
| 84 | THR84 | 0.29 | 0.36 |

SEQUENCE LISTING

<160> NUMBER OF SEQ ID NOS: 25

<210> SEQ ID NO 1
<211> LENGTH: 221
<212> TYPE: PRT
<213> ORGANISM: Artificial Sequence
<220> FEATURE:
<223> OTHER INFORMATION: Murine TF w 8 Hu residues

<400> SEQUENCE: 1

Gly Ile Pro Glu Lys Ala Phe Asn Leu Thr Trp Ile Ser Thr Asp Phe
1 5 10 15

Lys Thr Ile Leu Glu Trp Gln Pro Lys Pro Thr Asn Tyr Thr Tyr Thr
20 25 30

Val Gln Ile Ser Asp Arg Ser Arg Asn Trp Lys Asn Lys Cys Phe Ser
35 40 45

Thr Thr Asp Thr Glu Cys Asp Leu Thr Asp Glu Ile Val Lys Asp Val
50 55 60

Thr Trp Ala Tyr Glu Ala Lys Val Leu Ser Val Pro Arg Arg Asn Ser
65 70 75 80

Val His Gly Asp Gly Asp Gln Leu Val Ile His Gly Glu Glu Pro Pro
85 90 95

Phe Thr Asn Ala Pro Lys Phe Leu Pro Tyr Arg Asp Thr Asn Leu Gly
100 105 110

Gln Pro Val Ile Gln Gln Phe Glu Gln Asn Gly Arg Lys Leu Asn Val
115 120 125

Val Val Lys Asp Ser Leu Thr Leu Val Arg Lys Asn Gly Thr Phe Leu
130 135 140

Thr Leu Arg Gln Val Phe Gly Lys Asp Leu Gly Tyr Ile Ile Tyr Tyr
145 150 155 160

Arg Lys Gly Ser Ser Thr Gly Lys Lys Thr Asn Lys Thr Asn Thr Asn
165 170 175

Glu Phe Ser Ile Asp Val Glu Glu Gly Val Ser Tyr Cys Phe Phe Val
180 185 190

Gln Ala Val Ile Pro Ser Arg Lys Val Asn Arg Lys Ser Pro Asp Ser
195 200 205

```
Ser Thr Val Cys Thr Glu Gln Trp Lys Ser Phe Leu Gly
    210                 215                 220

<210> SEQ ID NO 2
<211> LENGTH: 118
<212> TYPE: PRT
<213> ORGANISM: Human
<220> FEATURE:
<221> NAME/KEY: BINDING
<222> LOCATION: (26)..(35)
<223> OTHER INFORMATION: CDR1
<220> FEATURE:
<221> NAME/KEY: BINDING
<222> LOCATION: (50)..(67)
<223> OTHER INFORMATION: CDR2
<220> FEATURE:
<221> NAME/KEY: BINDING
<222> LOCATION: (100)..(107)
<223> OTHER INFORMATION: CDR3

<400> SEQUENCE: 2

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Ser
            20                  25                  30

Trp Ile Ala Trp Val Arg Gln Met Pro Gly Lys Gly Leu Glu Trp Met
        35                  40                  45

Gly Gly Ile Ile Gly Pro Gly His Ser Tyr Thr Lys Tyr Ser Pro Ser
    50                  55                  60

Phe Gln Gly Gln Val Thr Ile Ser Ala Asp Lys Ser Ile Ser Thr Ala
65                  70                  75                  80

Tyr Leu Gln Trp Ser Ser Leu Lys Ala Ser Asp Thr Ala Met Tyr Tyr
                85                  90                  95

Cys Ala Arg Ile Asn Met Gly Tyr Phe Asp Tyr Trp Gly Gln Gly Thr
            100                 105                 110

Leu Val Thr Val Ser Ser
        115

<210> SEQ ID NO 3
<211> LENGTH: 111
<212> TYPE: PRT
<213> ORGANISM: Human
<220> FEATURE:
<221> NAME/KEY: BINDING
<222> LOCATION: (23)..(34)
<223> OTHER INFORMATION: CDR1
<220> FEATURE:
<221> NAME/KEY: BINDING
<222> LOCATION: (50)..(56)
<223> OTHER INFORMATION: CDR2
<220> FEATURE:
<221> NAME/KEY: BINDING
<222> LOCATION: (89)..(99)
<223> OTHER INFORMATION: CDR3

<400> SEQUENCE: 3

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Leu Lys Lys Phe
            20                  25                  30

Val Ser Trp Tyr Gln Gln Lys Pro Gly Gln Ala Pro Val Leu Val Ile
        35                  40                  45

Tyr Asp Asp Ser Asn Arg Pro Ser Gly Ile Pro Glu Arg Phe Ser Gly
    50                  55                  60
```

```
Ser Asn Ser Gly Asn Thr Ala Thr Leu Thr Ile Ser Gly Thr Gln Ala
 65                  70                  75                  80

Glu Asp Glu Ala Asp Tyr Tyr Cys Gly Thr Tyr Asp Gln Thr Ile Gly
                 85                  90                  95

His Asp Val Val Phe Gly Gly Gly Thr Lys Leu Thr Val Leu Gly
            100                 105                 110
```

<210> SEQ ID NO 4
<211> LENGTH: 116
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(105)
<223> OTHER INFORMATION: CDR3

<400> SEQUENCE: 4

```
Gln Val Gln Leu Val Gln Ser Gly Ala Glu Val Lys Lys Pro Gly Glu
 1               5                  10                  15

Ser Leu Lys Ile Ser Cys Lys Gly Ser Tyr Ser Phe Thr Ser Asn Trp
                20                  25                  30

Ile Gly Trp Val Arg Gln Met Pro Gly Lys Gly Leu Glu Trp Met Gly
             35                  40                  45

Trp Ile Tyr Pro Ser Asp Ser Met Thr Arg Tyr Ser Pro Ser Phe Gln
 50                  55                  60

Gly Gln Val Thr Ile Ser Ala Asp Lys Ser Ile Ser Thr Ala Tyr Leu
 65                  70                  75                  80

Gln Trp Ser Ser Leu Lys Ala Ser Asp Thr Ala Met Tyr Tyr Cys Ala
                 85                  90                  95

Arg Tyr Leu Phe Gly Leu Phe Asp Asn Trp Gly Gln Gly Thr Leu Val
            100                 105                 110

Thr Val Ser Ser
        115
```

<210> SEQ ID NO 5
<211> LENGTH: 107
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
<220> FEATURE:
<221> NAME/KEY: BINDING
<222> LOCATION: (88)..(95)
<223> OTHER INFORMATION: CDR3

<400> SEQUENCE: 5

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Gly Ser Tyr Tyr Val
                20                  25                  30
```

```
Ser Trp Tyr Gln Gln Lys Pro Gly Gln Ala Pro Val Leu Val Ile Tyr
        35                  40                  45

Asn Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Thr Tyr Asp Ser Ser Thr Asp Val
                85                  90                  95

Phe Gly Gly Gly Thr Lys Leu Thr Val Leu Gly
            100                 105

<210> SEQ ID NO 6
<211> LENGTH: 119
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(108)
<223> OTHER INFORMATION: CDR3

<400> SEQUENCE: 6

Gln Val Gln Leu Val Gln Ser Gly Ala Glu Val Lys Lys Pro Gly Glu
1               5                   10                  15

Ser Leu Lys Ile Ser Cys Lys Gly Ser Tyr Ser Phe Ser Asn Tyr Trp
            20                  25                  30

Ile Gly Trp Val Arg Gln Met Pro Gly Lys Gly Leu Glu Trp Met Gly
        35                  40                  45

Phe Ile Asp Pro Asp Asp Ser Asp Thr Asn Tyr Ser Pro Ser Phe Gln
 50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Ala Leu Tyr Met Gln Gly Gly Ser Phe Asp Ser Trp Gly Gln Gly
            100                 105                 110

Thr Leu Val Thr Val Ser Ser
        115

<210> SEQ ID NO 7
<211> LENGTH: 109
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
<220> FEATURE:
<221> NAME/KEY: BINDING
<222> LOCATION: (88)..(97)
<223> OTHER INFORMATION: CDR3

<400> SEQUENCE: 7
```

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Val
            20                  25                  30

Ser Trp Tyr Gln Gln Lys Pro Gly Gln Ala Pro Val Leu Val Ile Tyr
        35                  40                  45

Arg Asp Thr Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Val Ser Asn
                85                  90                  95

Gln Val Phe Gly Gly Gly Thr Lys Leu Thr Val Leu Gly
            100                 105
```

```
<210> SEQ ID NO 8
<211> LENGTH: 119
<212> TYPE: PRT
<213> ORGANISM: Human
<220> FEATURE:
<221> NAME/KEY: BINDING
<222> LOCATION: (26)..(34)
<223> OTHER INFORMATION: CDR1
<220> FEATURE:
<221> NAME/KEY: BINDING
<222> LOCATION: (49)..(65)
<223> OTHER INFORMATION: CDR2
<220> FEATURE:
<221> NAME/KEY: BINDING
<222> LOCATION: (98)..(108)
<223> OTHER INFORMATION: CDR3

<400> SEQUENCE: 8

Gln Val Gln Leu Val Gln Ser Gly Ala Glu Val Lys Lys Pro Gly Glu
1               5                   10                  15

Ser Leu Lys Ile Ser Cys Lys Gly Ser Tyr Ser Phe Thr Asn Ser Trp
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Ser Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Gly Ala Gly Tyr Gly Arg Met Phe Gly Asp Val Trp Gly Gln Gly
            100                 105                 110

Thr Leu Val Thr Val Ser Ser
        115
```

```
<210> SEQ ID NO 9
<211> LENGTH: 108
<212> TYPE: PRT
<213> ORGANISM: Human
<220> FEATURE:
<221> NAME/KEY: BINDING
<222> LOCATION: (23)..(33)
<223> OTHER INFORMATION: CDR1
<220> FEATURE:
<221> NAME/KEY: BINDING
<222> LOCATION: (49)..(55)
<223> OTHER INFORMATION: CDR2
```

```
<220> FEATURE:
<221> NAME/KEY: BINDING
<222> LOCATION: (88)..(96)
<223> OTHER INFORMATION: CDR3

<400> SEQUENCE: 9

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Ala
            20                  25                  30

Ser Trp Tyr Gln Gln Lys Pro Gly Gln Ala Pro Val Leu Val Ile Tyr
        35                  40                  45

Gln Asp Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Ala Tyr Thr Tyr Ser Thr Ser Trp
                85                  90                  95

Val Phe Gly Gly Gly Thr Lys Leu Thr Val Leu Gly
            100                 105

<210> SEQ ID NO 10
<211> LENGTH: 118
<212> TYPE: PRT
<213> ORGANISM: Human
<220> FEATURE:
<221> NAME/KEY: BINDING
<222> LOCATION: (26)..(37)
<223> OTHER INFORMATION: CDR1
<220> FEATURE:
<221> NAME/KEY: BINDING
<222> LOCATION: (52)..(67)
<223> OTHER INFORMATION: CDR2
<220> FEATURE:
<221> NAME/KEY: BINDING
<222> LOCATION: (100)..(107)
<223> OTHER INFORMATION: CDR3

<400> SEQUENCE: 10

Gln Val Gln Leu Lys Glu Ser Gly Pro Ala Leu Val Lys Pro Thr Gln
1               5                   10                  15

Thr Leu Thr Leu Thr Cys Thr Phe Ser Gly Leu Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Ser Asn Asp Lys Arg Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Lys Gln Glu Thr Ile Asp Tyr Trp Gly Gln Gly Thr
            100                 105                 110

Leu Val Thr Val Ser Ser
        115

<210> SEQ ID NO 11
<211> LENGTH: 105
<212> TYPE: PRT
<213> ORGANISM: Human
<220> FEATURE:
<221> NAME/KEY: BINDING
```

```
<222> LOCATION: (23)..(33)
<223> OTHER INFORMATION: CDR1
<220> FEATURE:
<221> NAME/KEY: BINDING
<222> LOCATION: (49)..(53)
<223> OTHER INFORMATION: CDR2
<220> FEATURE:
<221> NAME/KEY: BINDING
<222> LOCATION: (86)..(93)
<223> OTHER INFORMATION: CDR3

<400> SEQUENCE: 11
```

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Glu Lys Tyr Ala
            20                  25                  30

Tyr Trp Tyr Gln Gln Lys Pro Gly Gln Ala Pro Val Leu Val Ile Tyr
        35                  40                  45

Asp Asp Asn Asn Arg Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Ile Glu Ile Thr Val Phe Gly
                85                  90                  95

Gly Gly Thr Lys Leu Thr Val Leu Gly
            100                 105

```
<210> SEQ ID NO 12
<211> LENGTH: 112
<212> TYPE: PRT
<213> ORGANISM: Artificial sequence
<220> FEATURE:
<223> OTHER INFORMATION: Chimeric protein based on human sequence with
      bovine homolog residue substitutions

<400> SEQUENCE: 12
```

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Ile Ser Gly Cys Ser Ala Ile Glu Lys Thr Gln Arg
    50                  55                  60

Met Leu Ser Gly Phe Cys Pro His Lys Pro Ser Ala Lys Gln Val Ser
65                  70                  75                  80

Ser Glu Tyr Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

```
<210> SEQ ID NO 13
<211> LENGTH: 113
<212> TYPE: PRT
<213> ORGANISM: Artificial Sequence
<220> FEATURE:
<223> OTHER INFORMATION: Chimeric protein based on human sequence with
      pig homolog residue substitutions

<400> SEQUENCE: 13
```

Gly Pro Val Pro Pro Ser Thr Ala Leu Arg Glu Leu Ile Glu Glu Leu
1               5                   10                  15

```
Val Asn Ile Thr Gln Asn Gln Lys Ala Pro Leu Cys Asn Gly Ser Met
             20                  25                  30

Val Trp Ser Ile Asn Leu Thr Ala Gly Met Gln Tyr Cys Ala Ala Leu
         35                  40                  45

Glu Ser Leu Ile Asn Ile Ser Gly Cys Ser Ala Ile Glu Lys Thr Gln
     50                  55                  60

Arg Met Leu Ser Gly Phe Cys Ser His Lys Pro Ser Glu Gln Val
 65                  70                  75                  80

Pro Gly Lys His Ile Arg Asp Thr Lys Ile Glu Val Ala Gln Phe Val
                 85                  90                  95

Lys Asp Leu Leu Leu His Leu Lys Lys Leu Phe Arg Glu Gly Arg Phe
                100                 105                 110

Asn

<210> SEQ ID NO 14
<211> LENGTH: 112
<212> TYPE: PRT
<213> ORGANISM: Artificial Sequence
<220> FEATURE:
<223> OTHER INFORMATION: Chimeric protein based on human sequence with
      dog homolog residue substitutions

<400> SEQUENCE: 14

Gly Pro Val Pro Pro Ser Thr Ala Leu Arg Glu Leu Ile Glu Glu Leu
 1               5                  10                  15

Val Asn Ile Thr Gln Asn Gln Lys Ala Pro Leu Cys Asn Gly Ser Met
             20                  25                  30

Val Trp Ser Ile Asn Leu Thr Ala Gly Met Tyr Cys Ala Ala Leu Glu
         35                  40                  45

Ser Leu Ile Asn Val Ser Gly Cys Ser Ala Ile Glu Lys Thr Gln Arg
     50                  55                  60

Met Leu Ser Gly Phe Cys Ser Gln Lys Pro Ala Ala Gly Gln Ile Ser
 65                  70                  75                  80

Ser Glu Arg Ser Arg Asp Thr Lys Ile Glu Val Ala Gln Phe Val Lys
                 85                  90                  95

Asp Leu Leu Leu His Leu Lys Lys Leu Phe Arg Glu Gly Arg Phe Asn
                100                 105                 110

<210> SEQ ID NO 15
<211> LENGTH: 109
<212> TYPE: PRT
<213> ORGANISM: Artificial Sequence
<220> FEATURE:
<223> OTHER INFORMATION: Chimeric protein based on human sequence with
      mouse homolog residue substitutions

<400> SEQUENCE: 15

Gly Pro Val Pro Pro Ser Thr Ala Leu Arg Glu Leu Ile Glu Glu Leu
 1               5                  10                  15

Val Asn Ile Thr Gln Asn Gln Lys Ala Pro Leu Cys Asn Gly Ser Met
             20                  25                  30

Val Trp Ser Ile Asn Leu Thr Ala Gly Met Tyr Cys Ala Ala Leu Glu
         35                  40                  45

Ser Leu Ile Asn Ile Ser Gly Cys Ser Ala Ile Glu Lys Thr Gln Arg
     50                  55                  60

Met Leu Ser Gly Phe Cys Asn Arg Lys Ala Pro Thr Thr Val Ser Ser
 65                  70                  75                  80
```

```
Leu Pro Asp Thr Lys Ile Glu Val Ala Gln Phe Val Lys Asp Leu Leu
                85                  90                  95

Leu His Leu Lys Lys Leu Phe Arg Glu Gly Arg Phe Asn
            100                 105
```

<210> SEQ ID NO 16
<211> LENGTH: 129
<212> TYPE: PRT
<213> ORGANISM: Artificial Sequence
<220> FEATURE:
<223> OTHER INFORMATION: Human IL-4 with enhanced stability

<400> SEQUENCE: 16

```
His Lys Cys Asp Ile Thr Leu Gln Glu Ile Ile Lys Ser Leu Asn Ser
 1               5                  10                  15

Leu Thr Glu Gln Lys Ser Leu Cys Thr Glu Leu Thr Val Thr Asp Ile
            20                  25                  30

Phe Ala Ala Ser Lys Asn Thr Thr Glu Lys Glu Thr Tyr Cys Arg Ala
        35                  40                  45

Ala Thr Val Leu Arg Gln Tyr Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

<210> SEQ ID NO 17
<211> LENGTH: 109
<212> TYPE: PRT
<213> ORGANISM: Artificial Sequence
<220> FEATURE:
<223> OTHER INFORMATION: Human IL-13 with enhanced stability

<400> SEQUENCE: 17

```
Pro Pro Ser Thr Ala Leu Arg Glu Leu Ile Glu Glu Leu Val Asn Ile
 1               5                  10                  15

Thr Gln Asn Gln Lys Ala Pro Leu Cys Asn Gly Ser Met Val Trp Ser
            20                  25                  30

Ile Asn Leu Thr Ala Gly Met Tyr Cys Ala Ala Leu Glu Ser Leu Val
        35                  40                  45

Asn Val Ser Gly Cys Ser Ala Ile Glu Lys Thr Gln Arg Met Leu Ser
    50                  55                  60

Gly Phe Cys Pro His Lys Val Ser Ala Gly Gln Phe Ser Ser Leu His
65                  70                  75                  80

Val Arg Asp Thr Lys Ile Glu Val Ala Glu Phe Val Lys Asp Ile Ile
                85                  90                  95

Leu His Ile Lys Lys Leu Tyr Arg Glu Gly Arg Phe Asn
            100                 105
```

<210> SEQ ID NO 18
<211> LENGTH: 56
<212> TYPE: PRT
<213> ORGANISM: Homo sapiens

<400> SEQUENCE: 18

Lys Asp Leu Ile Tyr Thr Leu Tyr Tyr Trp Lys Ser Ser Ser Gly
1               5                   10                  15

Lys Lys Thr Ala Lys Thr Asn Thr Asn Glu Phe Leu Ile Asp Val Asp
            20                  25                  30

Lys Gly Glu Asn Tyr Cys Phe Ser Val Gln Ala Val Ile Pro Ser Arg
        35                  40                  45

Thr Val Asn Arg Lys Ser Thr Asp
    50                  55

<210> SEQ ID NO 19
<211> LENGTH: 56
<212> TYPE: PRT
<213> ORGANISM: Mus musculus

<400> SEQUENCE: 19

Lys Asp Leu Gly Tyr Ile Ile Thr Tyr Arg Lys Gly Ser Ser Thr Gly
1               5                   10                  15

Lys Lys Thr Asn Ile Thr Asn Thr Asn Glu Arg Ser Ile Asp Val Glu
            20                  25                  30

Glu Gly Val Ser Tyr Cys Phe Phe Val Gln Ala Met Ile Phe Ser Arg
        35                  40                  45

Lys Thr Asn Gln Asn Ser Pro Gly
    50                  55

<210> SEQ ID NO 20
<211> LENGTH: 112
<212> TYPE: PRT
<213> ORGANISM: Homo sapiens

<400> SEQUENCE: 20

Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Arg Phe Asn
            100                 105                 110

<210> SEQ ID NO 21
<211> LENGTH: 111
<212> TYPE: PRT
<213> ORGANISM: Sus scrofa

<400> SEQUENCE: 21

Gly Pro Val Pro Pro His Ser Thr Ala Leu Lys Glu Leu Ile Glu Glu
1               5                   10                  15

Leu Val Asn Ile Thr Gln Asn Gln Lys Thr Pro Leu Cys Asn Gly Ser
            20                  25                  30

Met Val Trp Ser Val Asn Leu Thr Thr Ser Met Gln Tyr Cys Ala Ala
        35                  40                  45

```
Leu Glu Ser Leu Ile Asn Ile Ser Asp Cys Ser Ala Ile Gln Lys Thr
            50                  55                  60

Gln Arg Met Leu Ser Ala Leu Cys Ser His Lys Pro Pro Ser Glu Gln
 65                  70                  75                  80

Val Pro Gly Lys His Ile Arg Asp Thr Lys Ile Glu Val Ala Gln Phe
                85                  90                  95

Val Lys Asp Leu Leu Lys His Leu Arg Met Ile Phe Arg His Gly
            100                 105                 110
```

<210> SEQ ID NO 22
<211> LENGTH: 111
<212> TYPE: PRT
<213> ORGANISM: Bos Taurus

<400> SEQUENCE: 22

```
Pro Val Pro Ser Ala Thr Ala Leu Lys Glu Leu Ile Glu Glu Leu Val
 1               5                  10                  15

Asn Ile Thr Gln Asn Gln Lys Val Pro Leu Cys Asn Gly Ser Met Val
                20                  25                  30

Trp Ser Leu Asn Leu Thr Ser Ser Met Tyr Cys Ala Ala Leu Asp Ser
            35                  40                  45

Leu Ile Ser Ile Ser Asn Cys Ser Val Ile Gln Arg Thr Lys Lys Met
         50                  55                  60

Leu Asn Ala Leu Cys Pro His Lys Pro Ser Ala Lys Gln Val Ser Ser
 65                  70                  75                  80

Glu Tyr Val Arg Asp Thr Lys Ile Glu Val Ala Gln Phe Leu Lys Asp
                85                  90                  95

Leu Leu Arg His Ser Arg Ile Val Phe Arg Asn Glu Arg Phe Asn
            100                 105                 110
```

<210> SEQ ID NO 23
<211> LENGTH: 109
<212> TYPE: PRT
<213> ORGANISM: Canis familiaris

<400> SEQUENCE: 23

```
Pro Val Thr Pro Ser Pro Thr Leu Lys Glu Leu Ile Glu Glu Leu Val
 1               5                  10                  15

Asn Ile Thr Gln Asn Gln Ala Ser Leu Cys Asn Gly Ser Met Val Trp
                20                  25                  30

Ser Val Asn Leu Thr Ala Gly Met Tyr Cys Ala Ala Leu Glu Ser Leu
            35                  40                  45

Ile Asn Val Ser Asp Cys Ser Ala Ile Gln Arg Thr Gln Arg Met Leu
         50                  55                  60

Lys Ala Leu Cys Ser Gln Lys Pro Ala Ala Gly Gln Ile Ser Ser Glu
 65                  70                  75                  80

Arg Ser Arg Asp Thr Lys Ile Glu Val Ile Gln Leu Val Lys Asn Leu
                85                  90                  95

Leu Thr Tyr Val Arg Gly Val Tyr Arg His Gly Asn Phe
            100                 105
```

<210> SEQ ID NO 24
<211> LENGTH: 110
<212> TYPE: PRT
<213> ORGANISM: Rattus rattus

<400> SEQUENCE: 24

-continued

```
Gly Pro Val Arg Arg Ser Thr Ser Pro Pro Val Ala Leu Arg Glu Leu
1               5                   10                  15

Ile Glu Glu Leu Ser Asn Ile Thr Gln Asp Gln Lys Thr Ser Leu Cys
                20                  25                  30

Asn Ser Ser Met Val Trp Ser Val Asp Leu Thr Ala Gly Gly Phe Cys
            35                  40                  45

Ala Ala Leu Glu Ser Leu Thr Asn Ile Ser Ser Cys Asn Ala Ile His
        50                  55                  60

Arg Thr Gln Arg Ile Leu Asn Gly Leu Cys Asn Gln Lys Ala Ser Asp
65                  70                  75                  80

Val Ala Ser Ser Pro Pro Asp Thr Lys Ile Glu Val Ala Gln Phe Ile
                    85                  90                  95

Ser Lys Leu Leu Asn Tyr Ser Lys Gln Leu Phe Arg Tyr Gly
                100                 105                 110

<210> SEQ ID NO 25
<211> LENGTH: 111
<212> TYPE: PRT
<213> ORGANISM: Mus musculus

<400> SEQUENCE: 25

Gly Pro Val Pro Arg Ser Val Ser Leu Pro Leu Thr Leu Lys Glu Leu
1               5                   10                  15

Ile Glu Glu Leu Ser Asn Ile Thr Gln Asp Gln Thr Pro Leu Cys Asn
                20                  25                  30

Gly Ser Met Val Trp Ser Val Asp Leu Ala Ala Gly Gly Phe Cys Val
            35                  40                  45

Ala Leu Asp Ser Leu Thr Asn Ile Ser Asn Cys Asn Ala Ile Tyr Arg
        50                  55                  60

Thr Gln Arg Ile Leu His Gly Leu Cys Asn Arg Lys Ala Pro Thr Thr
65                  70                  75                  80

Val Ser Ser Leu Pro Asp Thr Lys Ile Glu Val Ala His Phe Ile Thr
                    85                  90                  95

Lys Leu Leu Ser Tyr Thr Lys Gln Leu Phe Arg His Gly Pro Phe
                100                 105                 110
```

SOLUTION PHASE BIOPANNING METHOD USING ENGINEERED DECOY PROTEINS

The present application claims the benefit of priority to U.S. Provisional Application Ser. No. 60/565,674 and U.S. Provisional Application Ser. No. 60/565,633 filed Apr. 26, 2004 the contents of which are completely incorporated by reference. The application submitted herewith contains a Sequence Listing on computer readable disk which material is hereby incorporated by reference.

BACKGROUND OF THE INVENTION

1. Field of the Invention

The present invention relates to methods for the selection of antibodies which bind to selected epitopes utilizing phage display of antibody combinatorial libraries. The invention also relates to antibodies prepared by such methods.

2. Related Art

In the postgenomic era, efforts in drug development can now be focused on finding methods to specifically block the function of key proteins previously identified by such techniques as microarray analysis of mRNA expression levels in disease states. Proteomics is the new science encompassing understanding the way proteins interact with each other both in coordinated pathways and as binding partners. Structure activity relationships for proteins include the mapping of common domains and identifying three-dimensional conformations responsible for functions. Access to three-dimensional (3D) information on proteins has also become routine. For example the NCBI maintains public access to a tool called VAST which is a structure-structure similarity search service. It compares 3D coordinates of a newly determined protein structure to those in the molecular modeling database (MMDB) and the protein database (PDB).

Phage display technology describes an in vitro selection technique in which the polynucleotide sequence encoding a peptide or protein is genetically fused to a coat protein of a bacteriophage, resulting in display of the fused protein on the exterior of the phage virion, while the DNA encoding the fusion resides within the virion. This physical linkage between the displayed protein and the DNA encoding it allows screening of vast numbers of variants of the protein, each linked to its corresponding DNA sequence, by a simple in vitro selection procedure called "biopanning".

Phage, ribosome, yeast, and bacterial display libraries are tools for querying large numbers of proteins or peptides. Ribosome display is a method of translating mRNAs into their cognate proteins while keeping the protein attached to the RNA. The nucleic acid coding sequence is recovered by RT-PCR (Mattheakis, L. C. et al. 1994. Proc. Natl. Acad. Sci. USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based on fusion of the target to exported bacterial proteins that associate with the cell membrane or cell wall (Chen and Georgiou. 2002. Biotechnol Bioeng, 79:496-503).

As compared to hybridoma technology, phage and other antibody display methods afford the opportunity to manipulate selection against the antigen target in vitro and without the limitation of the possibility of host effects on the antigen or vice versa. One particular advantage of in vitro selection methods is the ability to manipulate selection procedures to obtain antibodies binding to diverse sites on the target protein.

While phage libraries simplify the retrieval of genetic material associated with functional attributes, multistep panning strategies are required to isolate the best candidate from the library. On the other hand, in those instances where structural information concerning the functional domain of a polypeptide ligand is known, it would be desirable to have a method to select antibodies or other binding partners such as peptides or proteins which bind to a ligand at specific defined domains. Domain or epitope directed pannings have become a routine way of selecting antibodies that bind to a target protein. Such selections have primarily been achieved by employing a stepwise selection of antibodies utilizing methods known variously as selective panning, de-selective panning, ligand capture, subtractive panning or pathfinder selection (Hoogenboom, H. R. et al (2000) supra).

In subtractive panning, target(s) with overlapping but not completely identical binding sites can be used to de-select unwanted binders. This strategy has been used to identify binders even to unknown antigens as in the use of normal cells to de-select binders to cancer cells. Alternatively, naturally occurring proteins with some common domains or structure are used in sequential or competition selection to obtain antibodies binding to sites that differ or are common among the related antigens. Typically, these studies have utilized naturally occurring proteins such as related chemokines or mutant H-ras proteins (Horn, I. R. et al. 1999, FEBS Lett. 463:115-120).

Ligand-capture directed panning is analogous to an ELISA sandwich assay in that an immobilized antibody to an irrelevant and non-adjacent epitope is used to capture and present the preferred binding face of the target ligand for phage panning (U.S. Pat. No. 6,376,170). Others have used competing antibodies to selectively mask the antigen at other than the desired target domain (Tsui, P. et al. 2002. J. Immunol. Meth. 263:123-132). Pathfinder technology uses monoclonal and polyclonal antibodies, as well as natural ligands conjugated directly or indirectly to horseradish peroxidase (HRP). In the presence of biotin tyramine these molecules catalyze biotinylation of phage binding in close proximity to the target antigen, allowing specific recovery of 'tagged' phage from the total population using streptavidin. In this way, phage binding to the target itself, or in its immediate proximity, are selectively recovered (Osborn, J. K. et al. 1998. Immunotechnol. 3: 293-302). The use of monoclonal antibodies to direct binding to alternate sites has also been termed "epitope walking" (Osborn, J. K. et al. 1998. supra).

These methods suffer from the drawback that an entire effort directed to obtaining and characterizing an undesirable binding partner must precede the effort to obtain a binding partner to the desired domain and that a specific epitope is not targeted. The present invention provides a novel method to obtain antibodies or ligand binding partners that bind to a selected epitope by incorporating a hybrid competitor protein into the panning selection process.

SUMMARY OF THE INVENTION

The present invention provides a novel method to select ligand-binding partners that bind to a preselected domain using an engineered decoy ligand in the panning process. The decoy ligand is designed so that it differs from the target protein only in the preselected domain that constitutes the putative binding site. The design of the decoy protein can be based on structural information derived from actual measurements, for example X-ray crystallographic data, or the design may be based on in silico information, data generated by computational modeling of three-dimensional structures.

When structural information is available, design of the decoy protein is simplified. When no structural information is available or is incomplete, modification of discreet regions of the sequence can be based on natural variants, such as species homologues, to create a decoy.

The invention further relates to nucleic acids coding for the decoy proteins of the invention useful for expressing the decoy proteins in a host cell or organism.

If used to transfect a host cell, the decoy protein may be expressed on the surface of the cell or as a secreted free protein which is recoverable from the cell growth medium. The decoy protein can be purified or used in a heterogeneous environment, such as that on a cell surface. During the biopanning step, the molar ratio of the target and decoy protein is maintained such that nonspecific and low affinity binders are de-selected and only binders to the target are recovered. In this way, protein-binding partners fused to their cognate genetic material are selected from a library for the ability to specifically bind the target protein at a binding site that is altered in the decoy protein and therefore is known to interact with the desired domain.

In another aspect of the invention, the method of selecting antibodies that bind a predetermined epitope may be used to convert the desirable properties of one therapeutic target antibody or ligand binder which has proved successful in one species, such as an animal model, directly to an analogous biotherapeutic for efficacious use in another species. Alternatively, human biologic medicines may be readily converted to analogues useful for treatment of other mammals with an analogous mechanism of action in the animal genus or species in which it is intended for use, e.g. cattle, swine, poultry, dogs, cats, or other agriculturally important or domestic animals. In one embodiment of this invention, the process is used to select antibodies that interact with a homolog protein in the same three-dimensional domain as does a reference antibody. This has particular application where, for example, a monoclonal antibody directed to particular region or epitope of a human antigen is known and it is desirable to regenerate binding ligands, for example human antibodies to the human target, to the same epitope. In another embodiment, the process is useful where an antibody exists that binds to an epitope of a human antigen and surrogate antibodies that react with the same epitope in the corresponding protein in another species, such as the mouse, are desired for research purposes. In this manner, anti-mouse antibodies that have properties similar to the parent anti-human antibody can be obtained.

Thus, in one aspect, the present invention is directed to a method for selecting a blocking polypeptide ligand binding partner from a library wherein the specific functional region of the ligand to be bound is predetermined, said method comprising the steps of a) determining the functional domain of the protein to be blocked b) analyzing the common structural features between the ligand and one or more species or functional homologs of that ligand, c) creating a decoy incorporating said common structural features of the ligand and the chosen homologs wherein the decoy has the common structural features in regions other than the functional domain to be blocked, and d) using said decoy in excess of the ligand binding partner for selecting binders that preferentially bind to the functional domain to be blocked.

In another aspect, the present invention is directed to a method for identifying a polypeptide which binds to a preselected epitope of a target protein, which comprises (a) providing a library of phage particles that express polypeptides on the surface of the phage particles (b) preparing a decoy protein which has changes in the amino acid sequences corresponding to the preselected epitope of the target protein (c) incubating the library of phage particles with the target protein to select phage particles with polypeptides that bind to the target protein (d) adding the decoy protein as a competitor in molar excess concentration to negatively select for phage particles specific for the preselected epitope (e) separating the phage particles that bind to the target protein from those that bind to the decoy protein and (f) recovering the phage particles bound to the target protein.

BRIEF DESCRIPTION OF THE DRAWINGS

FIG. 1 reflects a graphic representation of how phage displayed antibodies or other binding ligands can bind to a target protein and an engineered decoy protein with changes in a predetermined epitope in accordance with the invention. The decoy protein is represented by the hatched Epitope.

FIG. 2 shows the CDR sequences and framework assignments which comprise the variable region sequences (SEQ ID Nos: 2-11) for the lead candidate mTF binding Fabs.

FIG. 3 is a graph of the concentration dependence of binding of the Fabs selected by the method of the invention to the target protein (mTF, solid lines) and to the engineered decoy with two amino acid changes in the preselected epitope (hu/mTF, broken lines).

FIG. 4 is a graph showing the concentration versus relative fluorescent units for two selected Fabs binding murine tissue factor.

FIG. 5 is a multiple sequence alignment of the mature IL-13 homolog proteins derived from various species: Human (SEQ ID NO: 20), Pig (SEQ ID NO: 21), Bovine (SEQ ID NO: 22), Dog (SEQ ID NO: 23), Rat (SEQ ID NO: 24), and Mouse (SEQ ID NO: 25).

FIGS. 6A & B are the energy and area dimensions of hIL-4 derived from crystallographic data.

FIGS. 7A & B are the energy and area dimensions of hIL-13 calculated from the IL-4 derived crystallographic data.

ABBREVIATIONS

Abs antibodies, polyclonal or monoclonal
bFGF basic fibroblast growth factor
GM-CSF granulocyte-macrophage colony stimulating factor
IL interleukin
Mab monoclonal antibody
TF tissue factor
FIIV Factor IIV (inactive)
FIIVa Factor IIVa (activated)
FX Factor X (inactive)
FX Factor Xa (activated)

DETAILED DESCRIPTION

Definitions

By the term “antibody” is meant an immunoglobulin or immunoglobulin derived binding fragment. While all immunoglobulins do not bind antigen, it has been shown that fragments of antibodies can bind antigens, target polypeptides or proteins, and some other molecules. Thus, as used herein and “antigen binding fragments” include, but are not limited to: (i) the Fab fragment consisting of the variable (V) domains of an antibody heavy (H) and light (L) chain along with the respective constant (C) domains (VL-CL and VH-CH1 domains); (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments (vii) single chain Fv molecules (scFv), wherein a VH domain and a VL domain are linked by a peptide linker which allows the two domains to associate to form an antigen binding site; (viii) bispecific single chain Fv dimers and (ix) combinations and fusion proteins comprising the aforementioned, including but not limited to diabodies, multivalent or multispecific fragments or other engineered constructs capable of binding a target polypeptide and comprising an immunoglobulin derived fragment.

"Chimera" or "chimeric proteins" are those containing residues or domains from one or more species homolog proteins. For example, chimeric antibodies contain variable domains typically derived from a murine mAb fused to constant domains from a human immunoglobulin.

"Decoy" or "decoy protein" is the designed polypeptide incorporating a preselected or engineered domain which will be used for negative or positive selection of target ligand binding partners from a library of potential target binders.

"Epitope" is defined as the three-dimensional region of a target ligand which represents the unit of structure bound by a single antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. The epitope may lie within or encompass a previously described functional unit or structurally characterized protein domain, such as a receptor-binding domain or a fibronectin-like domain. Thus, when an epitope is a functional domain of a protein, when bound by the selected binding partner, results in the desired modulation of the function of the target ligand and which are antagonistic or agonistic to the function of the target ligand.

"Surrogate" means having the analogous biological function. A surrogate antibody will perform the analogous function, agonize or antagonize the activity of the target ligand, in a context or animal species different that the example antibody.

By "human" or any any other species antibody, e.g. human antibody, is meant to include antibodies having variable or, variable and constant regions, derived from or closely matching human or another species germline immunoglobulin sequences. The antibodies of the invention may include amino acid residues not encoded by germline immunoglobulin sequences (such as, but not limited to, mutations introduced by random or site-specific mutagenesis in vitro or by somatic mutation in vivo). Thus, as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to a human germline antibody. Human antibodies have been classified into groupings based on their amino acid sequence similarities, and this information is available online at various government and academic websites such as IMGT (International ImmunoGeneTics) or IgBlast at the NCBI (National Center for Biologic Information). Thus, using a sequence similarity search, an antibody with similar linear sequence can be chosen as a template to create "human antibodies". Murine germline sequences are also known and can be employed in a similar manner. As data related to the germline immunoglobulins of other species is collected and indexed, similar use may be made of those sequences for the production on non-human antibodies of the invention from phage display libraries or other collections of antigen-binding fragments by methods now known in the art.

In one aspect, the present invention involves the use of phage display and combinatorial peptide libraries. Phage display and combinatorial peptide libraries have evolved into powerful and adaptable techniques for exploring peptide and protein interactions. A phage library can be created by inserting a library of random oligonucleotides or a library of polynucleotides containing sequences of interest, such as from the B-cells of an immunized animal or human (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000. Immunol. Today 21(8) 371-8). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody libraries also can be created synthetically by selecting one or more human framework sequences and introducing collections of CDR cassettes derived from human antibody repertoires or through designed variation (Kretzschmar and von Ruden 2000, Current Opinion in Biotechnology, 13:598-602). The positions of diversity are not limited to CDRs but can also include the framework segments of the variable regions.

Other libraries useful in the practice of the invention include phage displayed libraries derived from non-human animals or engineered antibody libraries. An example of the former includes the use immunoglobulin derived libraries from the camelid species which are naturally devoid of light chains (Hamers-Casterman et al., 1993, Nature 363: 446-448; Gahroudi et al., 1997, FEBS Lett.) and, of the later, single domain antibodies which are derived from either a heavy or a light chain variable domain with binding ability as taught in U.S. Pat. No. 6,248,516.

Moreover, various types of phage or other display systems, ribosome, yeast, bacteria or animal cells, can be combined with peptide or antibody phage libraries in various endeavors to understand biology or discover new drugs or drug targets. For example, peptide phage display libraries can be used to interrogate antibody phage libraries. Using an elimination process, a combination of substrate phage display and substrate subtraction methods can be used to discover specificity differences between very closely related enzymes and this information can be utilized to create highly selective inhibitors (Ke, S-H, et al. 1997. J. Biol. Chem. 272 (26):16603-16609).

The bonding between ligands and receptors like antigens and antibodies, is dependent on hydrogen bonds, hydrophobic bonds, electrostatic forces, and van der Waals forces. These are all bonds of a weak, non-covalent nature, yet the association between antigen and antibody is known to be one of the strongest found in nature. Like antibodies, antigens can be multivalent, either through multiple copies of the same epitope, or through the presence of multiple epitopes that are recognized by multiple antibodies. Interactions involving multivalency can produce more stabilized complexes, however multivalency can also result in steric difficulties, thus reducing the possibility for binding. All antigen-antibody binding is reversible, however, and follows the basic thermodynamic principles of any reversible bimolecular interaction:

$$K_A \underset{k_{off}}{\overset{k_{on}}{\rightleftharpoons}} \frac{[Ab-Ab]}{[Ab]*[Ag]}$$

Where $K_A$ is the affinity constant, Ab and Ag are the molar concentrations of unoccupied binding sites on the antibody or antigen respectively, and Ab-Ag is the molar concentration of the antibody-antigen complex. The forward reaction is known as the "on rate" and the dissolution or back reaction is known as the "off rate".

For efficient interaction to occur between the antigen and the antibody, the epitope must be readily available for binding. Because antigen molecules exist in space, the epitope recognized by an antibody may be dependent upon the presence of a specific three-dimensional antigenic conformation (e.g. a unique site formed by the interaction of two native protein subunits), or the epitope may correspond to a simple primary sequence region. Such epitopes are described as "conformational" and "linear", respectively.

METHOD OF THE INVENTION

We have devised a method for isolating antibodies or other binding ligands that bind to a predetermined epitope by directed selection of phage-displayed antibodies using an engineered competitor protein (FIG. 1). The method relies on structural information about the target protein which is applied to the design of an appropriate decoy protein. This decoy protein is used as a competitor in antibody phage display to isolate the desired epitope-specific antibodies (FIG. 1).

The binding specificity of antibodies generated by the traditional method of immunizing animals is driven by a combination of the animal's immune system and the protein antigen. Thus, antibodies derived from immunization often interact with "immunodominant" epitopes that are different from the desired target epitopes. Existing methods of antibody selection using phage-displayed antibody libraries cannot be directed precisely to the epitope of interest. The disclosed method has the advantage of allowing very precise and effective direction of the selection toward antibodies specific for the targeted epitope.

The method of selecting antibodies that bind a predetermined epitope may be used to convert the desirable properties of one therapeutic target antibody or ligand binder (biotherapeutic) which has proved successful in one species, such as an animal model, directly to an analogous biotherapeutic for efficacious use in another species. Alternatively, human biologic medicines may be readily converted to analogues useful for treatment of other mammals, e.g. cattle, swine, poultry, dogs, cats, or other agriculturally important, domestic animals or rare animals or endangered species.

Among the 15 most common disease states affecting companion animals (dogs, cats, and horses) many are hormonal: diabetes mellitus in canines and felines, thyroid disorders in canines and felines, hypothyroidism in canines, hyperthyroidism in felines, Addison's disease and Cushing's disease in canines. Other diseases common to companion animals and other animals include osteoarthritis and various forms of cancer. Thus, there is the potential for successful human biologic therapies, such as anti-cancer and anti-inflammatory antibody therapies, to be converted to other species specific analogues. For example, the drug REMICADE (infliximab) which binds to a unique epitope on human TNFalpha, using the methods of the invention could be converted to an therapeutically effective drug for use in treating companion animals for TNFalpha mediated disorders common to that species of animal.

Selection of Binding Target Site

Each lymphocyte cell produces antibodies that are specific not to an antigen, but to an epitope. While an antigen is part of a foreign cell, particle, protein or molecule that is being recognized by the immune system and targeted by antibodies and/or cytotoxic T cells, an epitope is the binding site corresponding to an antigenic determinant on a protein. Polypeptides, lipids, nucleic acids and many other materials can also function as antigens. Immune responses may also be generated against smaller substances, called "haptens", if these are chemically coupled to a larger "carrier protein", such as bovine serum albumin or hemocyanin or other synthetic matrices. Haptens may be a variety of molecules such as drugs, simple sugars, amino acids, small peptides, phospholipids, or triglycerides. Antigens which elicit strong immune responses are said to be "strongly immunogenic". It has been empirically determined that an antigenic determinant, that which will illicit a clonal immune response, may be as few as 1 to 8 amino acids or 1 to 6 monosaccharides. Operationally the epitope recognized by the immunoglobulin derived from a clone (a monoclonal antibody) may encompass a larger and non-contiguous sequence on the surface of a protein.

When an epitope lies within a functional region of a protein, the effect of binding of antibodies to that protein will be to neutralize the function of the protein conferred by that structural feature thereof. This concept has proven to be the basis of therapeutic monoclonal antibodies. Therefore, the ability to reproducibly select antibodies or other binders to a specific epitope or protein domain would represent an advance in the art of protein therapeutic development.

Antibody epitope mapping is one way in which functional domains can be identified. Epitope mapping can be done with low or high resolution depending upon the objective. Low resolution mapping involves exposing a set of monoclonal antibodies to sequences on the surface of a native protein. The emphasis is on covering the entire surface of the target and identifying which sequences are important for function. Unlike lead mAb candidates, the antibodies used in the epitope mapping can be low affinity, should include both neutralizing and non-neutralizing mAbs, and, in this method, determination of the exact epitope is not usually necessary. Once the epitope has been identified to a particular desired resolution, competition assays with the antibody that produces the desired effect, usually neutralization of function, can be used to identify other binders to that region, for example, human antibodies able to compete with a murine antibody for a human target protein.

Sets of antibodies binding a target protein can be used in other ways to identify epitopes. For example, the antigen can be digested with proteases and the binding of the resulting fragments to the antibody determined in an ELISA format or by mass spectroscopy. The antigen-antibody complex can be digested with proteases and the proteolytic fragments identified by mass spectroscopy. In this case, the masking of proteolytic sites by the antibody identify the epitope.

There are other methods that have been used to identify the epitope of an antibody. Peptides can be synthesized that correspond to overlapping fragments of the entire sequence of an antigen and the binding of the antibody to these peptides can be determined in an ELISA format or using Surface Plasmon Resonance spectroscopy. NMR studies using isotopically labeled antigen can be used to identify which amino acids have changes in their magnetic environment upon antibody binding. Another technique is the measurement of thermal melting transition temperature. The crystal structure of the antigen-antibody complex can be determined and used to identify the epitope. Of these methods, crystallography is the most definitive followed by NMR studies.

An ELISA format utilizes washing steps to remove unbound materials prior to detection. In the case where the epitope is linear (the antibody recognizes only a single linear sequence of amino acids) the affinity of the antibody for a peptide fragment containing the epitope may be sufficiently high to detect binding. Where the epitope is conformational consisting of two or more non-contiguous amino acid sequences within the protein, the affinity of each individual sequence for the antibody may be low and not detected. Using surface plasmon resonance spectroscopy, binding to the peptides defining a conformational epitope may not be detected since the affinity for each peptide of the epitope may be low. If the off rate of the peptide is high, binding may not be detected.

Epitopes can also be identified on proteins using nuclear magnetic resonance (NMR). Applicants co-pending applications (U.S. Ser. No. 10/393,926) teaches a technique that identifies specific atoms (generally $H^1$, $C^{13}$ and $N^{15}$), and hence amino acid residues, based on their local environment. Complete assignment of most or all resonances can be done for large proteins given sufficient time and instruments of high enough resolution. This method is based on the observation that when an antibody binds to an antigen, the local environment of some amino acids is changed. Those amino acids that can be subject to the highest changes are those most involved with antibody contact. It is theoretically possible to identify an epitope by making all NMR assignments for both the antigen and the antibody in bound and unbound states and determining which amino acids have atoms shifted. The complexity of the NMR spectra of an antigen-antibody complex makes such an analysis extremely difficult and not applicable to routine epitope identification. However, applicants' method identifies protein epitopes using proteins enriched in either C13 or N15 amino acids in which precise identification of NMR signals is not always required. Multiple labeling of two or more different amino acids in the same protein can be used where resonances for the different amino acids were sufficiently distinct. For example, alpha-N15 alanine and epsilon-N15-lysine could be incorporated into one protein as could epsilon-N15 histidine and alpha-N15 leucine. The epitopes can be either the binding regions of antibodies or of the ligands. Further, molecular modeling or algorithms that predict surface-exposed sequences on proteins can assist in epitope identification.

An epitope also can be designed based on the primary amino acid sequence of the target in the absence of physical measurements of the target structure. For example, in proteins about 5-10 amino acids residues within about a 5-15 linear segment of the protein can be altered to create a variant decoy or chimeric target protein and binding measured to determine the epitope.

Homology among proteins is based on the similarity in base sequences of genes or amino acid sequences of proteins that denotes a common evolutionary origin. Generally, there will be a similarity of structure or function of proteins that is due to a common evolutionary origin. This is not always the case and divergent evolution and mutation may lead to proteins which have structural similarities but divergent functions or convergent functions from dissimilar structures; orthologs and paralogs, respectively. Homologue-scanning mutagenesis is a well-known strategy for identification of receptor-binding regions of a protein by substitution of analogous regions from homologous proteins in order to preserve the native three-dimensional structure of the original protein; e.g. the substitution of regions of human growth hormone with regions from pig growth hormone, human prolactin or human placental lactogen, followed by determination of binding constants for the constructs. These natural structural variants may be used to determine domains or epitopes within the domains useful in the construction of the appropriate decoy protein of the invention.

Decoy Construction

A "decoy protein" as used herein refers to a protein which differs in one or more structural features from a target protein at the specific domain encompassing the site or functional region to be bound. Therefore, the decoy can be a chimeric target protein or the decoy can be a naturally occurring protein, such as a species homolog, and the target ligand can be the engineered sequence that includes the preselected binding domain. In the process of the invention, the decoy binds low affinity and non-specific binders and, those binders complexed with the target which are retained, are thereby selected. In one aspect, the suitable structural homologue that can serve as a scaffold for accepting the target epitope can be an ortholog of the target protein. A structural homologue can also be another member of a multigene family.

With the evolution and warehousing of large amounts of 3-dimensional structure information from X-ray crystallography, NMR, and other techniques, information about protein structure can be readily retrieved or virtual structural information can be generated in a number of ways. The Bioinformatics Research Center at the University of Glasgow provides access to an internet site for describing and comparing protein structures using Topology of Protein Structure (TOPS) software (T P Flores, D S Moss and J M Thornton. 1994. Protein Engineering, 7:31-37). Protein coordinates—in the form of PDB like files, can be submitted to the server. The structure is converted to a simplified cartoon representation, called a TOPS representation, and then compared against a non-redundant subset of all known structures. The results are returned as a sorted list; showing the compression value, the record identification of the structures, and the common pattern using a value of 1 for a pair of identical structures and 0 for two structures with no common features.

MASS (Multiple Alignment by Secondary Structures) is based on a two-level alignment, using both secondary structure and atomic representation. The rationale behind this approach is that proteins are inherently composed of secondary structure elements (SSEs). These are the regions within a protein that provide its stabilizing scaffold, onto which the functional sites are grafted. Consequently, SSEs are evolutionarily highly conserved while mutations frequently occur at flexible loops, which are more difficult to align. MASS, is a highly efficient method for structural alignment of multiple protein molecules and detection of common structural motifs. Utilizing secondary structure information aids in filtering out noisy solutions and achieves efficiency and robustness. The advantage of MASS is that it is sequence order-independent and thus capable of detecting non-topological structural motifs in multiple alignments or subsets. Using MASS, one can guide protein-protein docking, which is a notoriously difficult problem. MASS is freely available at http://bioinfo3d.cs.tau.ac.il/MASS/. (Dror, O. et al. *Protein Science* (2003), 12:2492-250.)

The present invention employs the method of combining structure information with large libraries of protein-nucleic acid coding-expression systems to allow selection of antibodies to a unique epitope. As an example, a complex and specific epitope on the murine homolog of human tissue factor ("TF") was targeted. Existing antibodies in the art either do not inhibit mTF function or are not specific competitive inhibitors of Factor X binding to TF. The disclosed antibodies have these functions and therefore represent previously unavailable tools for evaluating the therapeutic potential for anti-TF antibodies that neutralize TF activity by inhibiting the activation of FX. In addition, these antibodies are valuable reagents for dissecting the role of TF in normal and pathogenic thrombotic inflammatory, angiogenic, neoplastic, and developmental processes.

Isolation of Epitope-Directed Antibodies or Other Binding Ligands

Three general approaches to isolation of epitope-directed antibodies or other binding ligands according to the invention are: (1) competition selection using display libraries of antibodies or other potential binding ligands; (2) non-competitive selection using display libraries followed by screening for differential binding activity; and (3) immunization of animals followed by screening for differential binding activity.

In competition selection using decoy proteins, the display library is selected for binding to a target protein in the presence of the decoy protein that is in molar excess over the target protein. The selectivity of recovered antibodies or binding ligands is confirmed by screening of the isolated antibodies or binding ligands for binding to the target protein and not to the decoy.

Thus, in one example of this method, a method for identifying a polypeptide which binds to a preselected epitope of a target protein is provided, which comprises (a) providing a library of phage particles that express polypeptides on the surface of the phage particles (b) preparing a decoy protein which has changes in the amino acid sequences corresponding to the preselected epitope of the target protein (c) incubating the library of phage particles with the target protein to select phage particles with polypeptides that bind to the target protein (d) adding the decoy protein as a competitor in molar excess concentration to negatively select for phage particles specific for the preselected epitope (e) separating the phage particles that bind to the target protein from those that bind to the decoy protein and (f) recovering the phage particles bound to the target protein and not the decoy.

Less preferred is the use of the native protein as the "decoy" to select for binding to the chimeric or mutant protein. In this case, the protein which contains the original scaffold protein is used in molar excess over the chimeric or mutant protein. The selectivity of recovered antibodies or binding ligands is confirmed by screening of the isolated antibodies or binding ligands for binding to the decoy target and target proteins and not to the scaffold protein.

In a two-step selection with a decoy protein, the display library is selected against the target protein. Recovered antibodies or other binding ligands are then screened (usually individually) for selective binding to the target protein and not to the decoy protein.

For the immunization approach using the decoy protein, animal species suitable for isolation of stable hybridomas producing monoclonal antibodies are immunized with the target protein. Hybridomas are generated and screened for the expression of an antibody that binds to the target antigen but does not bind to the decoy protein. The immunization approach can be combined with either of the above display strategies. Thus, mRNA from the immune cells (e.g., spleen or peripheral blood lymphocytes) is used to generate an antibody library which is then processed as described for either display approach. This approach is not limited to animals suitable for isolation of stable hybridomas.

Peptide libraries can be designed according to methods described in detail herein, and methods generally available to those in the art (see, e.g., U.S. Pat. No. 5,723,286 issued Mar. 3, 1998 to Dower et al.). In one aspect, commercially available phage display libraries can be used (e.g., RAPIDLIB' or GRABLIB', DGI BioTechnologies, Inc., Edison, N.J.; Ph.D. C7C Disulfide Constrained Peptide Library, New England Biolabs).

Antibody libraries are available from, e.g. Cambridge Antibody Technology, Morphosys, Affymax Research Institute, Palo Alto, Calif. A number of strategies have been devised for selecting a workable subset of binders for further analysis and affinity maturation. These include: blocking immunodominant epitopes by competitive deselection, rescue of a broader range of antibody specificities using an epitope-masking strategy, screening by capture lift, antibody-guided selection using capture-sandwich ELISA, proximity-guides (ProxiMol) antibody selection, isolation of human monoclonal antibodies using guided selection with mouse monoclonal antibodies, selecting antibodies to cell-surface antigens using magnetic sorting techniques, isolation of human tumor-associated cell surface antigen-binding scFvs, subtractive isolation of single-chain antibodies using tissue fragments, selection of antibodies based on antibody kinetic binding properties, selection of functional antibodies on the basis of valency (Antibody Phage Display. Methods and Protocols. IN: David W. J. Coomber, Ed. Methods in Molecular Biology. Humana Press. Vol. 178, December 2001 pps. 133-145).

Affinity enrichment of phage is based on slow dissociation rates of target binders. A slow dissociation rate is usually predictive of high affinity. In these examples of affinity enrichment, the continued incubation of the target phage and the target-binder phage is performed in the presence of a saturating amount of a known target binder or by increasing the volume of the incubation solution. In each case, the rebinding of dissociated target-binder phage is prevented, and with increasing time, target-binder phages of higher affinity are recovered.

The preincubation time and the preincubation conditions are optimized for each target-binder of interest. To monitor the effect of the varying conditions on affinity enrichment pilot experiments of panning are performed. After incubation of the target and the target-binder phage and transformation of the host cells, the host cells are plated out onto selective media and quantified. Determining the change in the number of colonies that survive provides an easy assessment tool to determine the degree of affinity enrichment. As the number of surviving colonies declines, the number of surviving weak binders is significantly diminished, leaving fewer target binders with higher affinity. For example, the loss of the number of surviving colonies, until only 1%, 0.1%, or 0.001% survive, indicates optimal conditions for enriching target binders that bind the target having higher affinity. In some circumstance, the number of surviving colonies could be limited to about 100 colonies for analysis by sequencing.

Depending on the diversity of the type of target binder library used, the number of target binders with a higher affinity may by less than 10.

The use of the above affinity-enrichment techniques allows for enrichment without necessarily performing additional rounds of panning. The affinity-enrichment techniques can be used alone or in combination. It is to be understood that the present invention could also use multiple rounds of panning to provide for affinity enrichment if desired.

Citations: All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2004); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2004); Colligan et al., Current Protocols in Protein Science, John Wiley & Sons, NY, N.Y., (1997-2004).

While having described the invention in general terms, the embodiments of the invention will be further disclosed in the following examples.

Example 1

Design and Production of the Chimeric Human/Murine Tissue Factor Protein

The MAb designated TF8-5G9 recognizes and binds to human Tissue Factor and prevents association of Factor X with TF or the TF/Factor VIIa complex (Ruf, W. and Edgington, T. S. 1991. Thromb. Haemost. 66:529-539). Based on analysis of the crystal structure of the TF8-5G9 Fab complexed with human TF, all of the residues that form the epitope recognized by the Fab fall between residues 149 and 204 of human TF. This region of the protein is also known to play an important role in the interaction of TF with Gla-domain FX (Ruf et al 1992). Fifteen specific residues between 149 and 204 of huTF are located appropriately to make significant energetic contributions to binding (Huang, et al. *J. Mol. Biol.* 275, 873-894). As illustrated in the sequence alignment below, when the extracellular domain sequences of human (GenPept Accession No. NP_001984) and murine TF (GenPept Accession No. NP_034301) are aligned between residues 149 and 204 of the human EC domain and the 152-207 of the murine EC domain, seven of the fifteen significant residues are identical (human residues K149, K165, K166, T167, T170, N171, Q190) while eight of the fifteen residues are different (human residue replaced by: Y156T, K169I, V192M, P194F, V198T, R200Q, K201N and D204G). Residues in bold represent residues that contribute significantly to stabilization of TF8-5G9:huTF complex. These residues have a delta free energy of binding of 1-4 kcal/mol or greater.

```
Human                                          (SEQ ID NO: 18)
149KDLIYTLYYWKSSSSGKKTAKTNTNEFLIDVDKGENYCFSVQAVI
PSRTVNRKSTD204

Mouse                                          (SEQ ID NO: 19)
152KDLGYIITYRKGSSTGKKTNITNTNERSIDVEEGVSYCFFVQAMI
FSRKTNQNSPG207
```

According to this analysis, a chimeric protein decoy protein could be constructed from the murine Tissue Factor coding sequence by making mutations of the unique TF8-5G9 contact residues on mTF to correspond to the residue found on huTF at the position according to the alignment. Although there are other positions where there are amino acid residue differences between murine and human tissue factor, these were assumed not to contribute to the overall function or structure of the protein in terms of the targeted epitope. Using the mTF gene as a template, a chimeric protein was constructed having mutations of the eight unique TF8-5G9 contact residues on mTF to the corresponding residue found on huTF (SEQ ID NO. 1). The membrane-spanning region was deleted so that only the soluble extracellular domain of TF was expressed and a carboxy-terminal His-tag was added to simplify purification. The soluble murine TF and the chimeric protein were expressed and purified from HEK 293E cells. Purified protein was analyzed by SDS-PAGE to show the expected MW for Hu/m TF (40 kDa) and for mTF (35 Kda).

Solution based panning with the HuCAL phage display library (Morphosys, Martinsried, Germany) was accomplished using biotinylated mTF protein. Chimeric hu/mTF protein was added as a decoy at a ten-fold molar excess to de-select phage specific for all epitopes except for the targeted epitope on mTF. Phage bound to biotinylated mTF were recovered by capture on streptavidin coated magnetic beads. All binders were sequenced to yield twenty-three unique Fabs from this panning: at the concentration tested, 9 recognized only mTF, 3 preferentially recognized mTF over hu/mTF, and 11 recognized the two proteins similarly (Table 1).

A panning on mTF without the chimeric protein competitor was performed to verify that the Fabs selected were the result of the epitope directed selection and not a hotspot on mTF. Panning conditions were identical between the two experiments except for the omission of the competing antigen in the selection process. All binders were sequenced to yield seven unique Fabs. Only one of the Fabs isolated in the panning without competitor bound specifically to mTF suggesting that addition of the competitor antigen allowed selection of Fabs that specifically recognize mTF and not the hu/mTF protein with changes in the TF8-5G9 epitope (Table 1).

TABLE 1

| Panning | Fab Clones Binding | | |
|---|---|---|---|
| Experiment | mTF >> h/m TF | mTF > hu/mTF | mTF = h/mTF |
| Competition (m/hTG = 10× mTF) | 9/23 | 3/23 | 11/23 |
| mTF only | 1/7 | 2/7 | 4/7 |

Figure 3:
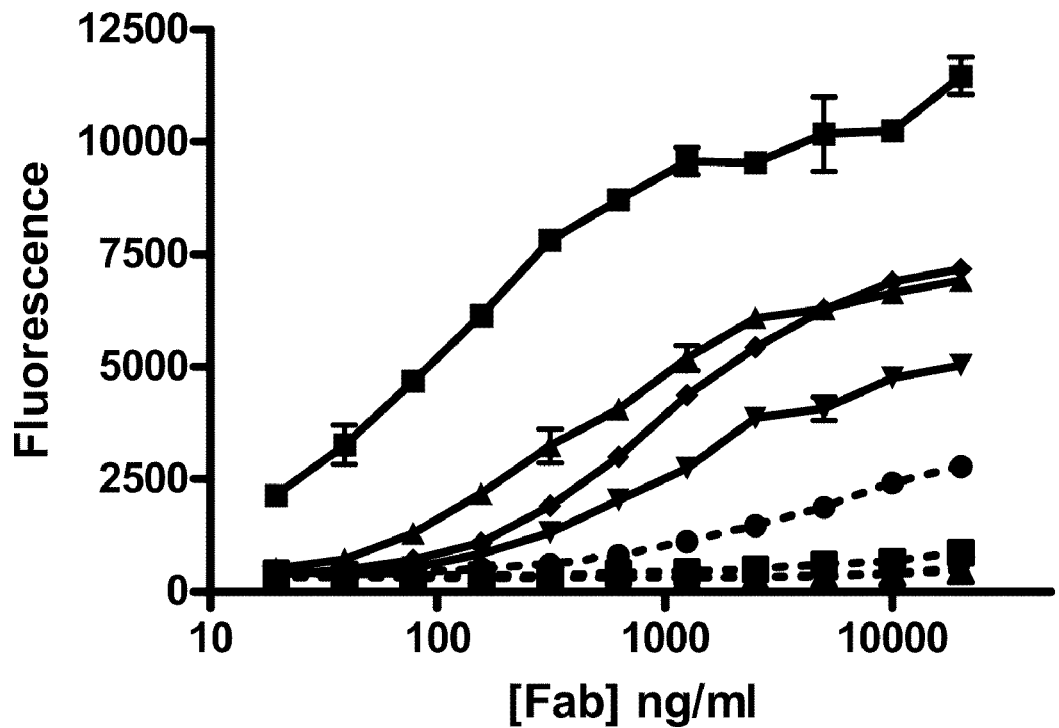

Human anti-murine TF specific Fabs were purified by affinity chromatography and evaluated for binding to mTF or hu/mTF by ELISA. The CDR sequences for these Fabs are listed in FIG. 2; framework assignments were made by comparison to the Morphosys HuCAL manual. Framework sequences are listed in the lower section of FIG. 2. All nine mTF specific Fabs demonstrated dose dependent binding to mTF with minimal cross reactivity to the hu/mTF (FIG. 3). In the Fab format, PHD127 had the highest binding affinity for mTF in this format while PHD103 had the lowest affinity. Five Fabs (PHD 103, 104, 126, 127, and 130) were selected for conversion into full-length immunoglobulins based on their affinity for mTF. The variable regions for the five Fabs (PHD 103, 104, 126, 127, and 130) are shown in FIG. 2 and SEQ ID NOS: 2-11 were cloned into vectors for expression of mIgG2a molecules in HEK 293 cells.

Inhibition of Coagulation

The selected anti-mTF surrogate Fabs were evaluated for their ability to inhibit coagulation in human plasma using murine brain extracts as a source of mTF. Based on previous experiments, Fabs that bind to the TF8-5G9 epitope on mTF are expected to interrupt the coagulation pathway and delay clot formation. In this assay, inhibition of fibrin clot formation was measured in human plasma. Four of the eight Fabs tested delayed or inhibited coagulation in human plasma in vitro: PHD 103, PHD 104, PHD 126 and PHD 127. PHD126 and PHD 127 were significantly more potent at inhibiting coagulation in human plasma. Based on the curve fit to the clotting time versus Fab concentration the measurable E50 values ranged from 0.2 µg/ml to 63 µg/ml.

TABLE 2

| Fab | EC50 Conc. (ug/ml) |
| --- | --- |
| PHD102 | >200 |
| PHD103 | 63.3 |
| PHD104 | 23.8 |
| PHD109 | >200 |
| PHD126 | 0.23 |
| PHD127 | 0.82 |
| PHD128 | >200 |
| PHD129 | >200 |

Factor X Inhibition

Factor X inhibition by those anti-mTF Fabs that inhibited coagulation (PHD 103, 104, 126, 127) was measured in the presence of murine brain extracts (as the source of tissue factor). Extracts were incubated with FVIIa, and anti-mTF surrogate Mabs were added in the presence of FX and inhibition of the conversion of FX to FXa was measured. PHD 103, 126 & 127 Fabs inhibited Factor X activation (cleavage) to Factor Xa. Inhibition of Factor X activation was subsequently reevaluated using the full-length anti-mTF IgGs. Good inhibition was observed for PHD 103, 126 and 127, while no inhibition was observed with PHD 104.

FACS Analysis

Figure 4:
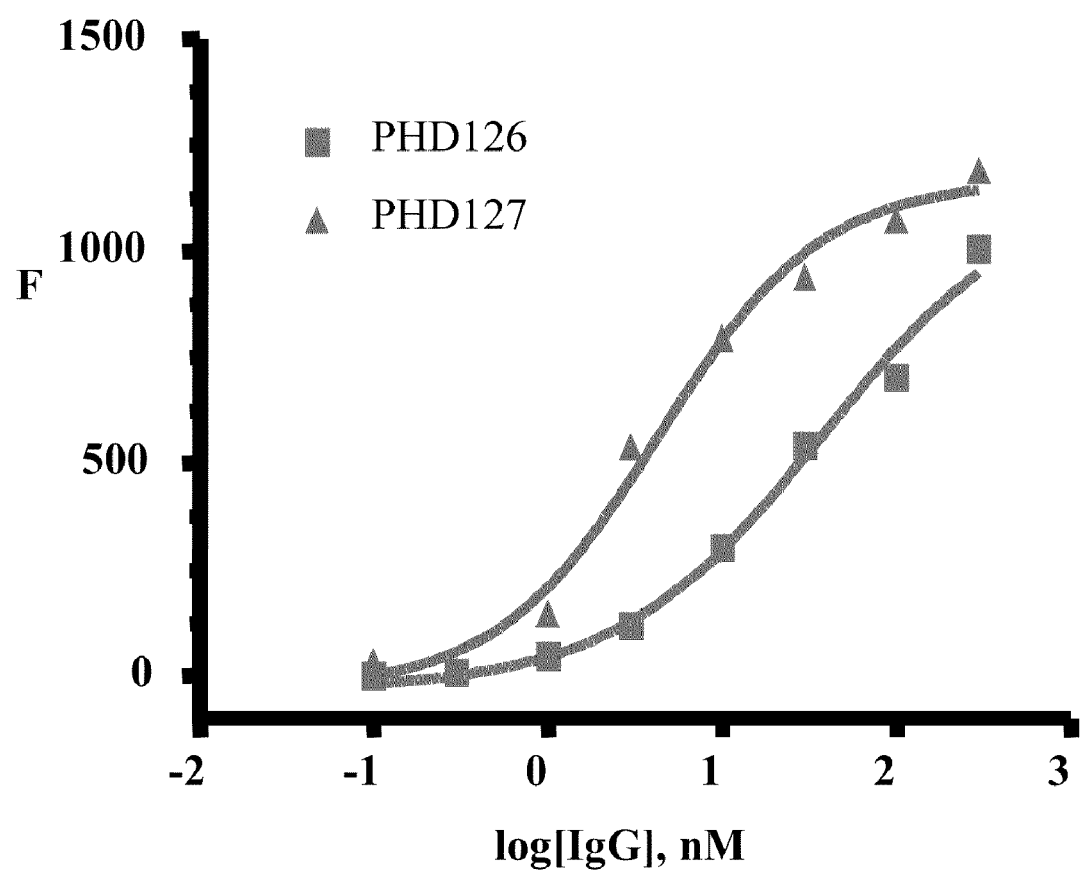

As the most active attractive candidate antibodies, PHD126 and PHD127 were evaluated for their ability to bind to B6F10 melanoma cells that express mTF at high levels. PHD126 and PHD127 bound cell-associated mTF in a dose dependent manner with an EC50 of 37.8 nM or 4.35 nM respectively (FIG. 4). The complete variable region sequences for PHD 126 and 127 heavy and light chains as shown by individual subdomain components in FIG. 2 are included as SEQ ID NOS: 6-9 as indicated.

SUMMARY

The experiments described herein demonstrate that epitope directed selection of phage-displayed antibodies using an engineered competitor protein is a viable process. The method relies on structural information about the target protein to allow the design of an appropriate competitor. In addition, this method allows for the selection of antibodies reactive to specific epitopes on a protein of interest. Existing methods of antibody selection using phage-displayed antibody libraries cannot be directed precisely to the epitope of interest. The disclosed method has the advantage of allowing very precise and effective direction of the selection toward antibodies specific for the targeted epitope. We have employed this method to allow selection of antibodies to a unique epitope on mTF.

TF is a complex molecule which functions both as a receptor and as an ligand, being capable of forming a unique complex with FVIIa and FX. Thus, Mabs that prevent this interaction must be directed to a unique region of the molecule. Existing antibodies in the art either do not inhibit mTF function or are not specific competitive inhibitors of Factor X binding to TF. The disclosed antibodies have these functions and therefore represent previously unavailable tools for evaluating the therapeutic potential for anti-TF antibodies that neutralize TF activity by inhibiting the activation of FX. In addition, these antibodies are valuable reagents for dissecting the role of TF in normal and pathogenic thrombotic inflammatory, angiogenic, neoplastic, and developmental processes.

Example 2

Construction of a Chimeric Decoy Protein for Selection of Binders to a Common Domain Capable of Activating Different Receptor Subunits Interleukin-13 (IL-13) is a cytokine that is found at elevated levels in the airways of patients with asthma. IL-13 is produced by activated CD4+ T cells and plays an important role in the B-cell proliferation and IgE production, goblet cell hyperplasia and mucus hypersecretion, eosinophilic inflammation, and airway hyperresponsiveness observed in asthma patients. Overexpression of IL-13 in transgenic mice has been shown to confer an asthma-like phenotype while neutralization of IL-13 using antagonists has been shown to attenuate the asthmatic response.

IL-13 binds to at least two receptors, one that can be found on most cell types except T cells, and the other that may function as a decoy receptor. The receptor that has been implicated in the pro-inflammatory responses is shared with the receptor for IL4 and is comprised of two subunits, IL4Ralpha1 and IL13Rbeta1. IL-13 is a member of the short chain cytokine family that includes IL-4, IL-2, IL-3, and GM-CSF. These proteins adopt a four-helix bundle topology and include two or three disulfide bonds. A solution structure for IL-13 has been determined verifying its similarity to other proteins in this family (Eisenmesser, E. Z., et al. J. Mol. Biol. (2001) 310:231-241; Moy, F. J., et al., J. Mol. Biol. (2001) 310:219-230). Although IL-13 shares only 25% sequence identity with IL-4, the overall structures are quite similar and it is expected that the interaction of IL-13 with its receptor will be similar to that recently determined for IL-4 and its receptor. Indeed, given that the two cytokines share one subunit in their receptors, it is likely that IL-13 and IL-4 will share structural similarities in their interactions with IL4Rα1. The three dimensional structure for IL-13 taken together with mutational studies indicates that there are two faces of the cytokine that play an important role in interacting with its receptor. The model suggests that the face of the protein comprised of helices A and C interacts with the IL4Ralpha1 subunit of the receptor and the helix A to helix D interface interacts with the IL13Ralpha1 subunit Based on the IL-13 structure and receptor interaction model, it is expected that an antibody that blocks the interaction of the A and D helices with IL13Ralpha1 or that blocks interactions between the A-C face and IL4Ralpha1 may be an excellent candidate for an anti-IL13 therapeutic. In an effort to direct antibody selection toward the receptor-interactive parts of IL-13, we have proposed preparing chimeric cytokine molecules. In these chimeric proteins, the loop connecting the C and D helices will be replaced with the corresponding sequence from the species to be used for immunization. In models, the C-D loop is the most surface exposed portion of the molecule and does not interact with the IL-13 receptor. In addition, this loop is quite flexible in the solution structures and is therefore likely to tolerate mutations without disrupting the overall topology of the molecule. In the resulting chimeric protein, one portion of the molecule will appear much like self to the host and is therefore less likely to induce a significant immune response. However, the part of the molecule that retains the fully human sequence will appear foreign to the host species and is likely to generate an immune response. Antibodies selected from the chimeric immunogens are expected to display neutralizing activity in human receptor based assays.

There is a need for potent antagonists of IL-13 to evaluate the benefit of its inhibition in human disease, particularly for asthma, and thereby as therapeutic agents. The novel IL-13 variants described herein are useful as immunogens for enhancing the generation of antagonist antibodies, as screening or selection agents to identify neutralizing antibodies, or as direct antagonists of native IL-13. In addition, development of potent and novel IL-13 agonists may be useful for targeting certain cancers that overexpress an IL-13 receptor on the cell surface (Hussain, S. R. and Puri, R. K., Blood (2000) 95:3506-351).

Novel analogs of IL-13 were constructed. These compounds may be considered as chimeras of human IL-13 and IL-13 from other species since they utilize partial sequences from multiple species. These mutants were rationally designed by incorporating amino acids from sequentially distinct regions of one species into the IL-13 sequence of human IL-13.

Based on the structural homology between the two cytokines a model for the IL-13: IL-13R1 complex was proposed. Using the NMR model for IL-13 (coordinate file: 1GA3) and the sequence of IL-13, analogs of IL-13 were constructed that are proposed to have utility as human IL-13 agonists, human IL-13 antagonists or as an immunogen or biopanning element for the generation of anti-human IL-13 antibodies.

The file 1GA3 available at http://www.ncbi.nlm.nih.gov/ contains an overlay of 20 NMR structures for IL-13. Observation of the structures indicated that, while the 4 helices are highly conserved, the N- and C-termini and the loop between the C and D helices are highly flexible, as evidenced by numerous conformations. The first structure in the file was used for analysis of designed IL-13 mutants that would retain both structure and activity.

There is a large loop between the C and D helices that is adjacent to the mostly buried B helix. This loop is a place where mutations may be accepted since it is distant from the A, C and D helices. The B loop is defined by amino acids $Met^{43}$ to $Asn^{53}$ and the CD loop is defined by amino acids $Cys^{71}$ to $Thr^{88}$. The end of the loop is difficult to assign but definitely ends by the beginning of helix D with $Glu^{91}$. In most structures the amino acids involved in the interaction between the B helix and the CD loop are:

B helix: $Cys^{45}$, $Leu^{48}$, $Glu^{49}$, $Leu^{51}$, possibly $Asn^{53}$, and $Val^{54}$ CD Loop: $Cys^{71}$, $Val^{75}$, $Lys^{74}$ (possible), $Val^{85}$, $Arg^{86}$ (possible) $Ile^{90}$ In addition, there are no hydrogen bonds in this region; $Pro^{72}$ is not involved but is essential for the turn, and there is a significant interaction between $Trp^{35}$ and loop residues between $Arg^{86}$ and $Lys^{89}$.

Residues in the B helix that interact with the C/D loop are $Leu^{48}$, $Leu^{51}$ and $Val^{54}$.

$Ala^{47}$ fills a pocket and may be able to be substituted. There are no hydrogen bonds between the CD loop and the B helix.

Residues in the B helix that interact with the A/B loop are $Met^{43}$, $Ala^{47}$ and $Ser^{50}$.

A Blast search of the NCBI was done to identify other species IL-13 with the following results (http://www.ncbi.nlm.nih.gov/entrez/query.fcgi?db=Protein):

```
Human IL-13                                                        (SEQ ID NO: 20)
GPVPPSTALRELIEELVNITQNQKA-
PLCNGSMVWSINLTAGMYCAALESLI
NVSGCCSAIEKTQRMLSGFCPH-
KVSAGQFSSLHVRDTKIEVAQFVKDLLLH
LKKLFREGRFN Sus Scrofa                                                         (SEQ ID NO: 21)
GPVPPHSTALKELIEELVNITQNQKT-
PLCNGSMVWSVNLTTSMQYCAALES
LINISDCSAIQKTQRMLSALCSHKPPSE-
QVPGKHIRDTKTIEVAQFVKDLL
KHLRMIFRHG Bos Taurus                                                         (SEQ ID NO: 22)
PVPSATALKELIEELVNTTQNQKV-
PLCNGSMVWSLNLTSSMYCAALDSLIS
ISNCSVIQRTKKMLNALCPHKPSAKQVS-
SEYVRDTKTEVAQFLKDLLRHSR
IVFPNERFN Canis                                                              (SEQ ID NO: 23)
PVTPSPTLKELIEELVNITQN-
QASLCNGSMVWSVNLTAGMYCAALESLINS
DCSAIQRTQRMLKALCSQKPAAGQISS-
ERSPJJTKIEVIQLVKNLLTYVRG
VYRHGNF Rat                                                                (SEQ ID NO: 24)
GPVTRRSTSPPVALRELIEEL-
SNITQDQKTSLCNSSMVWSVDLTAGGFCAA
LESLTNISSCNAIHRTQRILNGLCN-
QKASDVASSPPDTKIEVAQFISKLLN
YSKQLFRYG
```

-continued

```
Mouse                                                   (SEQ ID NO: 25)
GPVPRSVSLPLTLKELIEELSNITQDQT-
PLCNGSMVWSVDLAAGGFCVALD
SLTNISNCNAIYRTQRILHGLCNRKAPT-
TVSSLPDTKIEVAHFITKLLSYT
KQLFRHGPF
```

The sequences of human, bovine, pig, dog, rat and mouse IL-13 were aligned as shown (FIG. 5) using ClustalW algorithm within the Vector NTi Suite (InforMax, Inc., Bethesda, Md.).

The B helix sequences are given below with amino acids not identical to human are underlined. The residues at which interaction between the B helix and CD loop are predicted to interact are indicated by an asterisk in TABLE 3.

TABLE 3

| | |
|---|---|
| Human | M YCAALESLINV |
| Bovine | M YCAALDSLISI |
| Pig | MQYCAALESLINI |
| Dog | M YCAALESLTNV |
| Rat | GFCAALESLTNI |
| Mouse | GFCVALDSLTNI |
| Interacting | * ** * * |

These alignments suggest several sites at which amino acids may be substituted in the B helix and C/D loop of human IL-13 from other species, with retention of structural integrity and receptor binding activity. Using the residues from the B helix and the CD loop predicted to interact a strategy for preparation of chimeric proteins was devised where the CD loop residues from the human protein were replaced with the analogous residues from a different species. To maintain protein stability it was also necessary to replace the corresponding interacting residues from the B helix of the same species. In the case of bovine, pig, or mouse IL-13 the preferred embodiment necessitates changing only one amino acid, $Val^{54}$ to $Ile^{54}$ since all of the other interacting residues are identical to those found for the human protein.

Additional embodiments of the design include two substitutions in helix B from the mouse protein: $Glu^{49}$=>$Asp^{49}$ and $Ala^{46}$=>$Val^{46}$. $Tyr^{44}$ could also be replaced by Phe and $Leu^{51}$ could be replaced by Val. However, this last substitution is close to the C helix and could perturb its structure. The sequences in the C/D loop are for the six proteins are shown in Table 4 where residue positions predicted to interact with the B loop are indicated in the last row by an asterisk.

TABLE 4

| | |
|---|---|
| Human | CPHKVSAGQFSSLHVRDTKI |
| Bovine | CPHKPSAKQVSSEYVRDTKI |
| Pig | CSHKPPSEQVPGKHIRDTKI |
| Dog | CSQKPAAGQISSERSRDTKI |
| Rat | CNQKASDVASS PPDTKI |
| Mouse | CNRKAPTTVSS LPDTKI |
| Interacting | ** ** ** ** |

In the C/D loop there are numerous preferred changes that could be made based on homology. Many of these substitutions are unlikely to affect the overall loop conformation, however, the $Arg^{86}$ to Pro substitution in rat and mouse IL-13 proteins would indicate a significant difference in the structure of the C/D loop, as does the deletion of three amino acids for the mouse and rat proteins. Similarly the $Val^{75}$ to Pro mutation in bovine, pig and dog suggests significant conformational rearrangements. Additional embodiments of the design in this region include the $Ala^{46}$=>Val and $Glu^{49}$=>Asp mutations observed in the B helix of the mouse protein together with the $Val^{85}$=>Leu in the C/D loop.

The amino acids in the B helix and the C/D loop of the various species were substituted for the corresponding amino acids in the human sequence and five models built for each one using InsightII with high optimization however other modeling programs could be substituted.

Dog model: All five models constructed are of similar energy. Examination of the models shows that they are all quite similar, not only in the CD loop but also in the rest of the structure. Thus, substitution of the residues from canine to human IL-13 in helix B and the CD loop are expected to give a suitable chimeric protein.

Bovine model: All 5 models are of similar energy. There is considerable difference in the position of the side chains in 81-85 of all three models but the variation is no more significant than that observed for the 20 NMR models. The addition of the extra proline in the CD loop does not alter the conformation significantly. Thus, these substitutions are predicted to yield an acceptable chimera.

Pig Model: All five models are of similar energy. As with the bovine model, there are differences in the side chain positions of several amino acids in the loop but no significant backbone differences. The addition of the amino acid at the beginning of the B helix is well accommodated. Thus, this variant is predicted be an acceptable chimera.

Mouse model: With the deletion of three amino acids in the loop, all five models have significantly different conformations in the loop from the human model. All are of low energy; from an absolute energy comparison, these models are the lowest of all the chimeras. The overall topology of the four helices is largely unaltered however, and this variant is expected to be a suitable chimera.

All of these chimeras have reasonable conformations and should have very similar structures in the A, C and D helices. The sequences of the recommended chimeras are:

```
Human (native)
Human-Bovine                                          (SEQ ID NO: 12)
GPVPPSTALR ELIEELVNIT QNQKAPLCNG SMVWSINLTA GNYCAALESL Human-Pig                                             (SEQ ID NO: 13)
GPVPPSTALR ELIEELVNIT QNQKAPLCNG SMVWSINLTA GMYCAALESL Human-Dog                                             (SEQ ID NO: 14)
GPVPPSTALR ELIEELVNIT QNQKAPLCNG SMVWSTNLTA GMQYCAALESL Human-Mouse                                           (SEQ ID NO: 15)
GPVPPSTALR ELIEELVNIT QNQKAPLCNG SMVWSINLTA GMYCAALESL Human (native)
GPVPPSTALR ELIEELVNIT QNQKAPLCNG SMVWSINLTA GNYCAALESL Human-Bovine
INVSGCSAIE KTQRNLSGFC PHKVSAGQFS SLHVRDTKTE VAQFVKDLLL Human- Pig
INISGCSAIE KTQRNLSGFC PHKPSAKQVS SEYVPJJTKIE VAQFVKDLLL Human- Dog
INISGCSAIE KTQRMLSGFC SHKPPSEQVP GKHIRDTKIE VAQFVKDLLL Human-Mouse
INVSGCSAIE KTQRMLSGFC SQKPAAGQIS SERSRDTKIE VAQFVKDLLL INISGCSAIE KTQRNLSGFC NRKAPTTV   S    SLP        DTKIE
VAQFVKDLLLHuman               HLKKLFREGR FN Human-Bovine HLKKLFREGR FN Human-Pig    HLKKLFREGR FN Human-Dog    HLKKLFREGR FN Human-Mouse  HLKKLFREGR FN
```

The chimeric decoy proteins are provided in the sequence listing as SEQ ID NO: 12 (human-bovine), SEQ ID NO: 13 (human-pig), SEQ ID NO: 14 (human-dog), SEQ ID NO: 15 (human-mouse). One use of the chimeric proteins is for the selection of functionally neutralizing antibodies to human IL-13.

Antibodies can be recovered by antibody library screening/selection techniques such as antibody phage display. In another aspect, these chimeric IL-13 proteins are useful in the selection and/or screening of neutralizing antibodies. In one application, hybridomas recovered from animals immunized with IL-13 or one or more of these chimeras can be screened for binding to one or more of the chimeras not used for immunization, thus avoiding antibodies recognizing the C/D loop. In a second application, these chimeric proteins can be used in different combinations for the selection and screening of combinatorial antibody libraries, particularly phage display libraries. Based on the design consideration described herein, the selection or screening will suppress the identification of antibodies recognizing the C/D loop. Thus, both applications are expected to favor the isolation of neutralizing antibodies, particularly those recognizing the A, C and D helices that are fully conserved in the species variants and the constructed chimeric proteins.

A second use of these mutants is as antagonists to human IL-13. IL-13 is known to bind to two receptor subunits. The subtle changes in structure from human IL-13 introduced by the non-human amino acids in the two regions of the molecule can have an allosteric effect on the binding to either receptor subunit. By the selective abrogation of receptor subunit binding, a competitive antagonist is created.

Example 3

Calculations for Engineering Decoy Proteins Using NMR Data

This invention describes a new technique for the identification of epitopes on proteins using nuclear magnetic resonance (NMR). NMR is a technique that identifies specific atoms (generally H1, C13 and N15), and hence amino acid residues, based on their local environment. Carbon and nitrogen NMR spectra are less complex than proton spectra but natural abundance of the required nuclei can limit sensitivity. With large proteins, there can be a considerable amount of overlap in the spectra between atoms in similar environments. Complete assignment of most or all resonances can be done for large proteins given sufficient time and instruments of high enough resolution.

When an antibody binds to an antigen, the local environment of some amino acids is changed. Those amino acids that can be subject to the highest changes are those most involved with antibody contact. The strategy is to identify an epitope by making all NMR assignments for both the antigen and the antibody in bound and unbound states and determining which amino acids have atoms shifted. The complexity of the NMR spectra of an antigen-antibody complex makes such an analysis extremely difficult if not impossible with today's instruments and methods and is not applicable to routine epitope identification.

Protein epitopes can be identified using proteins enriched in either C13 or N15 amino acids in which precise identification of NMR signals is not always required. These epitopes could be either the binding regions of antibodies or of receptors.

Using recombinant technology, the protein is expressed in media in which a single amino acid has been replaced with its N15 or C13 labeled counterpart. The protein generated has the identical structure and activity as its unlabeled counterpart. An N15 or C13 NMR spectra is then run on the protein, both in the presence and absence of a binding antibody. The low natural abundance of the resonating nuclei of the unlabeled amino acids will simplify the spectra such that a decoupled spectra will exhibit singlets for N15 spectra and singlets or simple patterns for C13 depending on whether the amino acids was uniformly or specifically labeled. In those instances where the labeled amino acid is involved in binding with the antibody, a shift in resonance will be seen. As an example, if a protein of 200 amino acids contained 10 N15 labeled alanines, 10 singlets would be seen in the N15 spectra. If, when bound to the antibody, two of these were shifted, it would be because their local environment had been altered. From this, their location in the epitope could be inferred. The specific location of the two alanines in the sequence would not be known from this single spectrum. When the process had been repeated 20 times with a different amino acid labeled each time, the composition of the epitope would be known. Since the protein is being produced recombinantly, the sequence is known. From the epitope composition and protein sequence, the location of the epitope can be determined. Molecular modeling or algorithms that predict surface-exposed sequences on proteins can assist in epitope identification.

It need not be necessary to prepare 20 labeled proteins. Multiple labeling (2 or more different amino acids labeled in the same protein) could be used where resonances for the different amino acids were sufficiently distinct. For example, a-N15 alanine and e-N15-lysine could be incorporated into one protein as could 3-N15 histidine and a-N15 leucine.

This technique offers several advantages over the current procedures for epitope identification. Those methods using synthetic peptides (pin, spot or solution and ELISA or competition) or phage can miss conformational epitopes. This NMR procedure, since it uses the intact protein, will detect conformational epitopes as readily as linear epitopes. Variations of the spot synthesis (e.g. matrix of peptides) are claimed to be better at identifying conformational epitopes but the number of peptides required increases exponentially with the number of amino acids in the protein to the point that approximately 2 million peptides would be required for a protein of molecular weight 40 kD. Proteolysis, in combination with mass spectrometry, can identify some conformational epitopes but the technique is destructive to the protein and increasingly larger amounts of protein are needed for mass spec as the molecular weight increases. The NMR procedure is non-destructive. If the labeled protein is in short supply, it can be recovered after each experiment and reused to map another antibody. Point mutations or "alanine scans" of the protein can work well for the identification of both linear and conformational epitopes but the difficulties are that each protein requires its own DNA for expression, all point mutations are not secreted and it must be determined for each mutation that the protein is properly folded. The NMR procedure uses the same DNA for all labeled proteins and the labeled proteins secrete and fold identically to the unlabeled protein. Crystallography is the "gold standard" for epitope identification. Its drawbacks are the extensive amount of time involved, the amount of protein that can be required, the difficulty of growing a diffraction grade crystal and fact that each antibody to the same antigen requires new protein and a new crystal.

Example 4

Engineering of a Chimeric Decoy Protein Using Crystal Structure

Based on the crystal structure of IL-4 and a close analog, IL-13, a particular receptor binding domain was chosen as an antibody target. A chimeric protein was engineered for selection of binders to this region of both proteins.

The crystal structure of IL-4 has been solved. The crystal structure of IL-13 has not been determined but a theoretical molecular model has been constructed. Both IL-4 and IL-13 are therapeutically important proteins based on their biological functions. IL-4 has been shown to be able to inhibit autoimmune diseases, and IL-4 IL-13 both showed potentials to enhance anti-tumor immune responses. On the other hand, since both cytokines are involved in the pathogenesis of allergic diseases, antagonism of these cytokines would provide therapeutic benefits to allergy and allergic asthma.

Some mutant proteins (e.g. the IL-4 Y124D antagonist and the IL-13 R112D agonist, J. Biol. Chem (2000), 275, 14375-14380) have been described in the literature. Using molecular modeling, the following novel agonistic mutants of IL-4 and IL-13 were designed. Because they are predicted to be structurally more stable than the native proteins they are expected to be biologically more potent binders to the cytokine receptors and have potential as antineoplastic agents. Secondly, these proteins can be used as stable analogs of the native cytokines for solution phase panning procedures and with the intent of finding a domain selective binding agent, e.g. a receptor binding domain antagonist.

Using molecular modeling, the crystal structure of IL-4 and the theoretical model of IL-13 from the Brookhaven Crystallographic Database, the structures of IL-4 and IL-13 were examined. Several amino acids in the interior of the structures were identified to which substitutions could be made that would not be expected to adversely affect the structures. Indeed, energy calculations suggest that these structures could actually be more stable than the native sequences. The substitutions made for IL-4 were $Thr^{13}\Rightarrow Ser^{13}$, $Thr^{22}\Rightarrow Ser^{22}$, $Phe^{45}\Rightarrow Tyr^{45}$, $Phe^{55}\Rightarrow Tyr^{55}$ and for IL-13 $Ile^{48}\Rightarrow Val^{48}$, $Gln^{90}\Rightarrow Glu^{90}$, $Leu^{95}\Rightarrow Ile^{95}$, $Leu^{96}\Rightarrow Ile^{96}$, $Leu^{99}\Rightarrow Ile^{99}$, $Phe^{103}\Rightarrow Tyr^{103}$.

A database was created (FIGS. 6A & 6B) for IL-4 that contained calculations of the exposed amino acids. The first column contains data for side chains only and the second column contains data for both side chain and backbone. Amino acids with little or no surface exposed area are shown in bold/blue.

The buried residues were extracted from the table and cysteines removed since they cannot be replaced without compromising the structure. The result of possible substitutions is calculated below:

| | FR SIDE | FR TOTAL | Possible Replacements | Energy Increase (Base is 603.493 kcal/mol) |
|---|---|---|---|---|
| 7 LEU7 | 0.04 | 0.03 | | |
| 10 ILE10 | 0.00 | 0.00 | | |

-continued

| | FR SIDE | FR TOTAL | Possible Replacements | Energy Increase (Base is 603.493 kcal/mol) |
|---|---|---|---|---|
| 11 ILE11 | 0.09 | 0.07 | | |
| 13 THR13 | 0.00 | 0.00 | Ser | 607.457/ |
| 14 LEU14 | 0.00 | 0.00 | | |
| 17 LEU17 | 0.01 | 0.04 | | |
| 22 THR22 | 0.01 | 0.10 | Ser | 606.487 |
| 25 THR25 | 0.07 | 0.05 | | |
| 29 VAL29 | 0.01 | 0.03 | | |
| 32 ILE32 | 0.01 | 0.06 | | |
| 45 PHE45 | 0.04 | 0.03 | Tyr, His | 609.651/652.501 |
| 47 ARG47 | 0.06 | 0.04 | | |
| 48 ALA48 | 0.02 | 0.01 | Ser, Val(?) | 684.427/1355.443 |
| 49 ALA49 | 0.00 | 0.00 | Ser | 662.543 |
| 51 VAL51 | 0.02 | 0.03 | | |
| 52 LEU52 | 0.00 | 0.00 | Ile | 642.620 |
| 55 PHE55 | 0.02 | 0.04 | Tyr | 612.756 |
| 56 TYR56 | 0.07 | 0.06 | | |
| 76 HIS76 | 0.02 | 0.02 | | |
| 79 LEU79 | 0.03 | 0.02 | | |
| 80 ILE80 | 0.09 | 0.07 | | |
| 83 LEU83 | 0.00 | 0.00 | | |
| 86 LEU86 | 0.00 | 0.00 | | |
| 87 ASP87 | 0.04 | 0.03 | Asn | 1139.982 |
| 90 LEU90 | 0.00 | 0.00 | | |
| 93 LEU93 | 0.02 | 0.04 | | |
| 94 ALA94 | 0.00 | 0.03 | Ser | 660.925 |
| 109 LEU109 | 0.00 | 0.00 | | |
| 112 PHE112 | 0.00 | 0.01 | Tyr | 855.581 |
| 113 LEU113 | 0.04 | 0.03 | | |
| 116 LEU116 | 0.02 | 0.02 | | |
| 120 MET120 | 0.00 | 0.00 | | |

The structure for IL-4 was minimized with 100 cycles of conjugate gradient, dielectric 100, with all hydrogens using Tripos force field and Kollman-Uni charges. The single changes proposed above were then made and the energy calculated. Base on these calculations, the best substitutions would be Ser for $Thr^{13}$, Ser for $Thr^{22}$, Tyr for $Phe^{45}$ and Tyr for $Phe^{55}$.

The crystal structure of IL-4 was recalled, the energy calculated before minimization, the four substitutions above made and energy recalculated with the following results:

Native Crystal Structure

| | |
|---|---|
| Bond Stretching Energy | 231.645 |
| Angle Bending Energy | 298.910 |
| Torsional Energy | 453.633 |
| Out of Plane Bending Energy | 46.674 |
| 1-4 van der Waals Energy | 386.851 |
| van der Waals Energy | 1134.199 |
| 1-4 Electrostatic Energy | 30.608 |
| Electrostatic Energy | 1043.112 |
| Total Energy | 3625.631 kcals/mol |

$Ser^{13}$, $Ser^{22}$, $Tyr^{45}$, $Tyr^{55}$ Structure

| | |
|---|---|
| Bond Stretching Energy | 233.378 |
| Angle Bending Energy | 299.147 |
| Torsional Energy | 449.605 |
| Out of Plane Bending Energy | 46.468 |
| 1-4 van der Waals Energy | 384.334 |
| van der Waals Energy | 1125.512 |
| 1-4 Electrostatic Energy | 30.677 |
| Electrostatic Energy | 1043.004 |
| Total Energy | 3612.126 kcals/mol |

There are decreases in torsional energy, 1-4 van der Waals and van der Waals energy. Based on energy calculations, this structure is predicted to be more stable than the native sequence. The amino acids modified are on the interior of the molecule but, since substitutions were evaluated for their ability not to perturb the secondary structure, the surface topology and hence the functional activity should be unchanged.

A similar table was constructed for IL-13 (FIGS. 7A & 7B). The crystal structure has not been published but a theoretical model is available. Ten cycles of minimization were conducted on both the initial structure and the modified one.

| | FR SIDE | FR TOTAL | Possible Replace-ments | Energy Increase (Base is 1725.421 kcal/mol) |
|---|---|---|---|---|
| 6 LEU6 | 0.06 | 0.07 | | |
| 9 LEU9 | 0.03 | 0.02 | | |
| 13 LEU13 | 0.00 | 0.03 | | |
| 17 THR17 | 0.00 | 0.03 | Ser | 1987.449 |
| 44 LEU44 | 0.07 | 0.05 | | |
| 47 LEU47 | 0.03 | 0.02 | | |
| 48 ILE48 | 0.08 | 0.06 | Val | 1722.283 |
| 50 VAL50 | 0.06 | 0.05 | Ile | 1841.982 |
| 51 SER51 | 0.00 | 0.00 | Thr | 2080.486 |
| 52 GLY52 | — | 0.00 | | |
| 63 LEU63 | 0.00 | 0.00 | | |
| 66 PHE66 | 0.04 | 0.04 | Tyr/His | 1995.898/1766.541 |
| 69 HIS69 | 0.01 | 0.01 | | |
| 72 SER72 | 0.04 | 0.03 | | |
| 73 ALA73 | 0.02 | 0.01 | | |
| 77 SER77 | 0.00 | 0.01 | | |
| 90 GLN90 | 0.02 | 0.04 | Glu | 1730.812 |
| 92 VAL92 | 0.01 | 0.01 | Ile | 9159.549 |
| 95 LEU95 | 0.00 | 0.01 | Ile | 1631.393 |
| 96 LEU96 | 0.00 | 0.00 | Ile | 1619.286 |
| 99 LEU99 | 0.03 | 0.03 | Ile | 1628.907 |
| 103 PHE103 | 0.01 | 0.01 | Tyr | 1624.121 |

Although Tyr for Phe66 has a high energy, it looks like a good substitution. The higher energy is due to higher van der Waals interactions of the hydroxyl.

Phe66 and His69 interact (π-π). Both must remain aromatic.

The Ile substitution for Val92 gives a high energy but a small amount of minimization drastically reduces it. It is probably an acceptable substitution.

Tyr for Phe103 adds an additional hydrogen bond with His69 and would be a good substitution.

The structure for IL-13 was recalled, energy calculated, substitutions made and energy recalculated to give the following results:

Initial Modeled Structure

| | |
|---|---|
| Bond Stretching Energy | 290.164 |
| Angle Bending Energy | 390.042 |
| Torsional Energy | 388.721 |
| Out of Plane Bending Energy | 30.217 |
| 1-4 van der Waals Energy | 286.329 |
| van der Waals Energy | 210.384 |

-continued

| | |
|---|---|
| 1-4 Electrostatic Energy | 27.906 |
| Electrostatic Energy | −1.547 |
| Total Energy | 1622.216 kcals/mol |

$Val^{48}$, $Glu^{90}$, $Ile^{95}$, $Ile^{96}$, $Ile^{99}$, $Tyr^{103}$

| | |
|---|---|
| Bond Stretching Energy | 288.604 |
| Angle Bending Energy | 383.273 |
| Torsional Energy | 384.452 |
| Out of Plane Bending Energy | 29.889 |
| 1-4 van der Waals Energy | 284.920 |
| van der Waals Energy | 228.808 |
| 1-4 Electrostatic Energy | 27.989 |
| Electrostatic Energy | −1.594 |
| Total Energy | 1626.342 kcals/mol |

There is a decrease in bond stretching energy, angle bending energy, 1-4 van der Waals and van der Waals energy with an increase in torsional energy and bond stretching energy. These latter interactions could be reduced by a repositioning of the newly placed Ile side chains.

Modified Structure

| Energy kcals/mol | RMS Force kcals/mol A | max Force kcals/mol A | Iteration count | Eval count | CPU Time | time |
|---|---|---|---|---|---|---|
| 1626.342 | 25.436 | 243.087 | 0 | 1 | 0 | 0:00:00.33 |
| 1326.768 | 14.851 | 134.040 | 1 | 8 | 0 | 0:00:01.11 |
| 1207.892 | 10.799 | 137.468 | 2 | 14 | 0 | 0:00:01.78 |
| 1121.012 | 10.155 | 171.991 | 3 | 20 | 0 | 0:00:02.44 |
| 1065.839 | 7.613 | 105.188 | 4 | 26 | 0 | 0:00:03.11 |
| 1031.513 | 6.361 | 73.260 | 5 | 32 | 0 | 0:00:03.76 |
| 995.717 | 6.643 | 64.166 | 6 | 38 | 0 | 0:00:04.42 |
| 965.486 | 5.399 | 54.345 | 7 | 44 | 0 | 0:00:05.09 |
| 945.615 | 5.429 | 61.839 | 8 | 50 | 0 | 0:00:05.76 |
| 924.480 | 4.655 | 50.214 | 9 | 56 | 0 | 0:00:06.42 |
| 907.908 | 4.448 | 55.866 | 10 | 62 | 0 | 0:00:07.08 |

WARNING: Maximum number of iterations (10) reached

Energy for Molecule: Interleukin-13 Model 1 (Theoretical Model)

| | |
|---|---|
| Bond Stretching Energy | 49.661 |
| Angle Bending Energy | 297.149 |
| Torsional Energy | 328.222 |
| Out of Plane Bending Energy | 8.774 |
| 1-4 van der Waals Energy | 189.249 |
| van der Waals Energy | 8.139 |
| 1-4 Electrostatic Energy | 28.271 |
| Electrostatic Energy | −1.556 |
| Total Energy | 907.908 kcals/mol |

Avg. Number of van der Waals+electrostatic pairs=5677

Avg. Number of 1-4 van der Waals+electrostatic pairs=3415

Avg. Number of scaled van der Waals+electrostatic pairs=248

| | Number | CPU Time (secs) | % of Total |
|---|---|---|---|
| Non Bonded Rebuilds | 2 | 0.08 | 1.08 |
| Energy Evaluations | 64 | 7.33 | 98.92 |

Initial Structure

Energy for Molecule: Interleukin-13 Model 1 (Theoretical Model)

| Energy kcals/mol | RMS Force kcals/mol A | max Force kcals/mol A | Iteration count | Eval count | CPU Time | time |
|---|---|---|---|---|---|---|
| 1622.189 | 25.201 | 243.087 | 0 | 1 | 0 | 0:00:00.34 |
| 1328.927 | 14.694 | 132.377 | 1 | 8 | 0 | 0:00:01.12 |
| 1212.237 | 10.675 | 135.392 | 2 | 14 | 0 | 0:00:01.79 |
| 1127.031 | 10.061 | 169.922 | 3 | 20 | 0 | 0:00:02.47 |
| 1072.925 | 7.499 | 103.477 | 4 | 26 | 0 | 0:00:03.13 |
| 1039.540 | 6.289 | 73.212 | 5 | 32 | 0 | 0:00:03.81 |
| 1004.102 | 6.619 | 64.355 | 6 | 38 | 0 | 0:00:04.49 |
| 973.968 | 5.370 | 54.031 | 7 | 44 | 0 | 0:00:05.15 |
| 954.110 | 5.428 | 64.203 | 8 | 50 | 0 | 0:00:05.82 |
| 932.787 | 4.648 | 46.556 | 9 | 56 | 0 | 0:00:06.50 |
| 915.954 | 4.442 | 52.618 | 10 | 62 | 0 | 0:00:07.16 |

WARNING: Maximum number of iterations (10) reached

Energy for molecule: Interleukin-13 Model 1 (Theoretical Model)

| | |
|---|---|
| Bond Stretching Energy | 48.807 |
| Angle Bending Energy | 300.150 |
| Torsional Energy | 331.002 |
| Out of Plane Bending Energy | 8.945 |
| 1-4 van der Waals Energy | 192.067 |
| van der Waals Energy | 8.307 |
| 1-4 Electrostatic Energy | 28.178 |
| Electrostatic Energy | −1.503 |
| Total Energy | 915.954 kcals/mol |

Avg. Number of van der Waals+electrostatic pairs=5717

Avg. Number of 1-4 van der Waals+electrostatic pairs=3426

Avg. Number of scaled van der Waals+electrostatic pairs=247

| | Number | CPU Time (secs) | % of Total |
|---|---|---|---|
| Non Bonded Rebuilds | 2 | 0.08 | 1.07 |
| Energy Evaluations | 64 | 7.41 | 98.93 |

Using molecular modeling, the crystal structure of IL-4 and the theoretical model of IL-13 from the Brookhaven Crystallographic Database, the structures of IL-4 and IL-13 were examined. Several amino acids in the interior of the structures were identified to which substitutions could be made that would not be expected to adversely affect the structures. Indeed, energy calculations suggest that these structures could actually be more stable than the native sequences. The substitutions made for IL-4 were $Thr^{13}$⇒$Ser^{13}$, $Thr^{22}$⇒$Ser^{22}$, $Phe^{45}$⇒$Tyr^{45}$, $Phe^{55}$⇒$Tyr^{55}$ and for IL-13 Ile$^{48}$⇒Val$^{48}$, Gln$^{90}$⇒Glu$^{90}$, Leu$^{95}$⇒Ile$^{95}$, Leu$^{96}$⇒Ile$^{96}$, Leu$^{99}$⇒Ile$^{99}$, Phe$^{103}$⇒Tyr$^{103}$.

The complete sequences are:

```
IL-4 Construct                                          (SEQ ID NO: 16)
HKCDITLQEI IKSLNSLTEQ KSLCTELTVT DIFAASKNTT EKETYCRAAT VLRQYYSHHE
KDTRCLGATA QQFHRHKQLI RFLKRLDRNL WGLAGLNSCP VKEANQSTLE NFLERLKTIM
REKYSKCSS IL-13 Construct                                         (SEQ ID NO: 17)
PPSTALRELI EELVNITQNQ KAPLCNGSMV WSINLTAGMY CAALESLVNV SGCSAIEKTQ
RMLSGFCPHK VSAGQFSSLH VRDTKIEVAE FVKDIILHIK KLYREGRFN
```

Where the underlined amino acids indicate the substitutions.

The lower energy of the modified structure after minor minimization suggests that this structure is more stable than the parent sequence. These constructs and others prepared in an analogous manner may be used in the method of the invention.

What is claimed is:

1. A method for identifying a polypeptide which binds to a preselected epitope of a target protein, which comprises:
   a) providing a library of phage particles that express polypeptides on the surface of the phage particles;
   b) preparing a decoy protein which has about 5-10 changes in the amino acid sequences within about a 5-15 linear segment of the target protein corresponding to the preselected epitope of the target protein;
   c) incubating the library of phage particles with the target protein to select phage particles with polypeptides that bind to the target protein;
   d) adding the decoy protein as a competitor in molar excess concentration to negatively select for phage particles specific for the preselected epitope;
   e) separating the phage particles that bind to the target protein from those that bind to the decoy protein and
   f) recovering the phage particles bound to the target protein.

2. The method of claim 1, where the decoy is used to select a subset of binders from the library for testing prior to deselecting binding to the target protein.

3. The method of claim 1, where the target protein is used to select a subset of binders from the library prior to deselecting those binders binding to the decoy.

4. The method according to claim 1, in which the polypeptide which binds to a preselected epitope is an antibody or an antibody fragment.

5. The method according to claim 4, in which the polypeptide is an antibody fragment comprising a Fab, Fab', or F(ab')2 fragment or derivative thereof.

6. The method according to claim 4, in which the monoclonal antibody is a surrogate antibody which binds the analogous epitope on murine tissue factor as does the murine anti-human tissue factor designated TF8-5G9 ATCC HB9382.

* * * * *